United States Patent
Kawasaki et al.

(10) Patent No.: US 9,180,216 B2
(45) Date of Patent: Nov. 10, 2015

(54) ELECTRON BEAM IRRADIATION DEVICE WITH GRIPPING/MOVING MEANS

(71) Applicant: Airex Co., Ltd., Nagoya-shi, Aichi (JP)

(72) Inventors: Koji Kawasaki, Nagoya (JP); Daisuke Kakuda, Nagoya (JP); Jun Masudome, Nagoya (JP)

(73) Assignee: Airex Co., Ltd., Nagoya-shi (JP)

(*) Notice: Subject to any disclaimer, the term of this patent is extended or adjusted under 35 U.S.C. 154(b) by 0 days.

(21) Appl. No.: 14/399,426

(22) PCT Filed: May 14, 2013

(86) PCT No.: PCT/JP2013/063364
§ 371 (c)(1),
(2) Date: Nov. 6, 2014

(87) PCT Pub. No.: WO2013/175997
PCT Pub. Date: Nov. 28, 2013

(65) Prior Publication Data
US 2015/0108366 A1    Apr. 23, 2015

(30) Foreign Application Priority Data
May 21, 2012    (JP) .................. 2012-115308

(51) Int. Cl.
*A61L 2/08*    (2006.01)
*G21K 5/04*    (2006.01)
(Continued)

(52) U.S. Cl.
CPC . *A61L 2/007* (2013.01); *A61L 2/08* (2013.01); *A61L 2/087* (2013.01); *A61L 2/26* (2013.01); *G21K 5/04* (2013.01); *G21K 5/10* (2013.01); *A61L 2202/23* (2013.01)

(58) Field of Classification Search
CPC ............. A61L 2/087; A61L 2/08; A61L 2/00; A61L 2/007; A61L 2/26; B65B 55/08; G21K 5/10; G21K 5/04; G21K 5/08
USPC ............. 250/492.3, 455.11, 492.1, 453.11, 250/491.1, 493.1; 422/186; 204/157.15; 315/111.81
See application file for complete search history.

(56) References Cited

U.S. PATENT DOCUMENTS 7,459,706 B2* 12/2008 Fontcuberta et al. ...... 250/492.3
8,278,632 B2* 10/2012 Nishino et al. ............. 250/491.1
(Continued)

FOREIGN PATENT DOCUMENTS

JP    11-248892    9/1999
JP    11-248894    9/1999
(Continued)

OTHER PUBLICATIONS

International Search Report for PCT/JP2013/063364 (English translation).

*Primary Examiner* — David A Vanore
(74) *Attorney, Agent, or Firm* — Quarles & Brady LLP; Gavin J. Milczarek-Desai

(57) ABSTRACT

An electron beam irradiation device which can irradiate an electron beam uniformly to an entire outer surface of an object of irradiation by using a small-sized low-energy electron accelerator with a narrow irradiation window is provided. The device has electron beam irradiation means forming an electron beam irradiation zone and gripping/moving means gripping a part of an object of irradiation and causing the object of irradiation to pass through the electron beam irradiation zone, and the whole surface of the object of irradiation can uniformly pass through the electron beam irradiation zone by combining re-gripping of the object of irradiation by two gripping mechanisms provided on the gripping/moving means, rotation of the object of irradiation by two rotation mechanisms, and movement of the object of irradiation by two moving mechanisms.

7 Claims, 20 Drawing Sheets

(51) Int. Cl.
*A61L 2/00* (2006.01)
*G21K 5/10* (2006.01)
*A61L 2/26* (2006.01)

(56) References Cited

U.S. PATENT DOCUMENTS

| | | | |
|---|---|---|---|
| 8,293,173 B2 * | 10/2012 | Bufano et al. | 422/22 |
| 8,330,120 B2 * | 12/2012 | Nishino et al. | 250/455.11 |
| 8,373,138 B2 * | 2/2013 | Nishino et al. | 250/455.11 |
| 8,461,550 B2 * | 6/2013 | Nishino et al. | 250/455.11 |
| 8,618,503 B2 * | 12/2013 | Nishino et al. | 250/455.11 |
| 8,790,589 B2 * | 7/2014 | Cirri et al. | 422/292 |
| 2003/0218414 A1 * | 11/2003 | Avnery | 313/359.1 |
| 2005/0161614 A1 * | 7/2005 | Bilstad et al. | 250/455.11 |
| 2010/0209290 A1 * | 8/2010 | Cirri et al. | 422/22 |
| 2011/0012030 A1 * | 1/2011 | Bufano et al. | 250/492.3 |
| 2011/0101248 A1 * | 5/2011 | Nishino et al. | 250/492.3 |
| 2015/0108366 A1 * | 4/2015 | Kawasaki et al. | 250/453.11 |

FOREIGN PATENT DOCUMENTS

| | | |
|---|---|---|
| JP | 2003-142392 | 5/2003 |
| WO | 03-041136 | 5/2003 |

* cited by examiner

Fig. 1
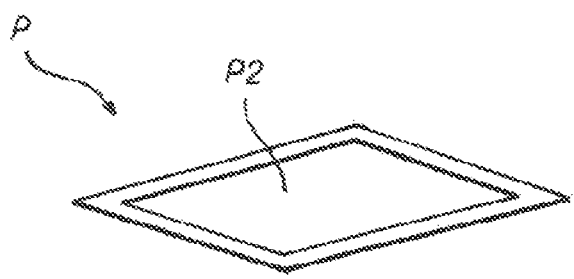
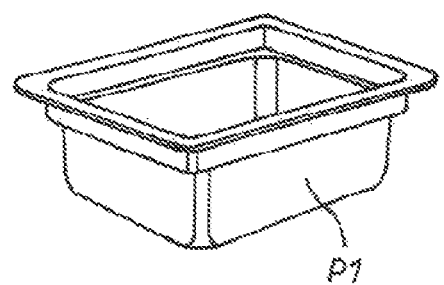

ELECTRON BEAM IRRADIATION DEVICE WITH GRIPPING/MOVING MEANS

TECHNICAL FIELD

The present invention relates to an electron beam irradiation device which sterilizes an outer packaged surface of a package accommodating a sterilized article with electron beam irradiation and conveys this sterilized package to a work room under an aseptic environment.

BACKGROUND ART

For convenience at medical sites, pre-filled syringes and pre-filled vials filled with pharmaceuticals in advance and the like are manufactured. A work for filling pharmaceuticals in these syringes and vials is performed in a filling work room under an aseptic environment (hereinafter referred to as an aseptic work room). The individual syringes and vials and the like used in this work are small, and the large quantity is needed to be treated. Thus, these syringes and vials and the like are sterilized by γ-ray irradiation, electron beam irradiation, EOG (ethylene oxide gas) and the like in the respective manufacture stages and carried into the aseptic work room in a state collected in a predetermined number and accommodated in a package.

This type of package includes a medical instrument package proposed in the following Patent Literature 1 or described as a prior art (see FIG. 1) and the like. These packages are generally called peel-open packages and are provided with a plastic tab molded in conformity with the shape of an article such as a syringe or a vial to be accommodated therein and an air-permeable upper-surface seal. For this upper-surface seal, an unwoven cloth made of high-density polyethylene extremely thin fibers, Tyvek (registered trademark) is generally used, and air can permeate the inside of the plastic tab through fine holes of this Tyvek (registered trademark), but intrusion of microorganisms is prevented.

The package configured as above is further packed on an outer part thereof with packing paper and distributed/transported. However, during distribution or transportation, or when it is taken out of the packing bag in order to be carried into the aseptic work room, the plastic tab and the outer packaged surface of the upper surface seal are contaminated. Therefore, the package cannot be carried into the aseptic work room unless the contaminated outer packaged surface is sterilized. Thus, the plastic tab and the outer packaged surface of the upper surface seal are sterilized by a sterilizing device provided continuously to the aseptic work room and then, carried into the aseptic work room, the upper surface seal is peeled open from the plastic tab in the aseptic work room, and a filling work is performed into the sterilized syringes and vials therein.

For these sterilizing devices, various methods such as EOG (ethylene oxide gas), hydrogen peroxide low-temperature gas, ozone gas, plasma, γ-ray irradiation, UV-ray irradiation, electron beam irradiation and the like are employed in accordance with the purpose. One of the most widely-used methods among them is the method by using hydrogen peroxide low-temperature gas.

In the method by using hydrogen peroxide low-temperature gas, a sterilization effect at a required level can be obtained, but certain treatment time is needed to sterilize the entire package, and if the hydrogen peroxide low-temperature gas intrudes into the plastic tab through the upper surface seal made of Tyvek (registered trademark), time for removing the hydrogen peroxide coagulated inside is required, which is a problem.

Thus, in the sterilizing device requiring treatment of a large quantity of articles per unit time as manufacture of a pre-filled syringe, a method with high sterilization effect in a short-term treatment is in demand. Thus, in the following Non-Patent Literature 1, a sterilizing device incorporating a low-energy electron accelerator is introduced as a safe device which can obtain a higher sterilization effect and higher productivity with no remaining substance as compared with general devices using hydrogen peroxide low-temperature gas.

This sterilizing device is actually operated for treatment of the package accommodating the prefilled syringes, and the package with the syringe subjected to sterilization treatment in advance therein is sterilized on its outer packaged surface with an electron beam and conveyed to the aseptic work room by a conveyer. This device performs irradiation by three low-energy electron accelerators arranged by an angle of 120 degrees from each other to the whole surface of the package from three directions (see FIG. 9).

In this device, the plastic tab and the upper surface seal can be efficiently sterilized by controlling a dose of the irradiated electron beam. According to the following Non-Patent Literature 1, 3600 syringes per hour can be treated by this device, and high productivity is realized.

CITATION LIST

Patent Literature

Patent Literature 1: Japanese Patent No. 4237489

Non-Patent Literature

Non-Patent Literature 1: Radiation Application Development Association, Radiation Application Technology Database, Data No. 010306 (prepared on Oct. 3, 2007 by Masayuki Sekiguchi)

SUMMARY OF INVENTION

Technical Problem

In the sterilizing device in the above described Non-Patent Literature 1, in order to sterilize the whole outer packaged surface of the medical instrument package, the electron beam is irradiated at the same time from the three low-energy electron accelerators arranged at an angle of 120 degrees from each other on an outer peripheral portion side of the medical instrument package to be conveyed in an advancing direction (see FIG. 9).

However, in this method, it is sufficient to irradiate the electron beam to the outer peripheral portion of the medical instrument package but it is not sufficient to irradiate the electron beam in a longitudinal direction of the medical instrument package, and there is a problem that reliability and safety of the sterilization effect cannot be kept high easily. Thus, if the electron beam is to be irradiated to the longitudinal direction of the medical instrument package from the outer peripheral portion, a distance from an irradiation window of each of the electron accelerators becomes large, and irradiation intensity needs to be made stronger through adjustment of the irradiation angle by enlarging the irradiation window of each of the electron accelerators and by raising an acceleration voltage of each of the electron accelerators. In such a case, a usage limit (life) by usage cumulative time of the electron accelerator with a raised acceleration voltage becomes short, and a maintenance cost of the device is raised, which is a problem.

Moreover, if the medical instrument package in the longitudinal direction is to be sufficiently sterilized by enhancing irradiation intensity of each of the electron accelerators, a strong point and a weak point of the irradiation intensity are generated depending on a portion in the medical instrument package, excessive irradiation by the electron beam is performed on the outer peripheral portion with a short distance from the irradiation window of the electron accelerator, and damage is caused in the medical instrument package. Moreover, in this case, there is a problem that the sterilization level is different depending on the portion of the medical instrument package.

On the other hand, in order to irradiate the electron beam from the outer peripheral portion of the medical instrument package, an irradiation width of the irradiation window of each of the three low-energy electron accelerators needs to be wider than an irradiated width of the corresponding medical instrument package in use. A price of a unit of the low-energy electron accelerator having an irradiation window wider than the irradiated width of the medical instrument package in general use is high, and a maintenance cost caused by replacement due to the usage limit (life) by the usage cumulative time is also high. Therefore, there is a problem that operation of the three expensive devices at the same time raises both an initial cost and the maintenance cost of the device.

In response to that and due to expansion of application of electron beam irradiation, many types of electron accelerators including particularly a small-sized low-energy electron accelerator with a narrower irradiation window width are manufactured. In general, if the width of the irradiation window is narrow, the device price becomes lower in the low-energy electron accelerators. Moreover, if the size of the electron accelerator becomes small, the electron beam irradiation device itself becomes compact, and both the initial cost and the maintenance cost of the device including the cost of the electron accelerator can be reduced.

However, if the low-energy electron accelerator having an irradiation window narrower than the width of the medical instrument package in use is used, the whole outer packaged surface of the medical instrument package cannot be sterilized. Moreover, if more than three electron accelerators are used, the initial cost and the maintenance cost of the device cannot be kept low as compared with the prior-art methods.

Thus, in order to solve the above described problems, the present invention has an object to provide an electron beam irradiation device which can irradiate an electron beam uniformly to an entire outer surface of an object of irradiation by using a small-sized low-energy electron accelerator with a narrow irradiation window, maintain reliability and safety of a sterilization effect high by making a sterilization level of each portion substantially equal, keep the initial cost and the maintenance cost of the device low, and extend the cost and a usage limit (life) of the electron accelerator.

Solution to Problem

In order to solve the above described problems, as the result of keen researches, the inventors have found that the electron beam can be uniformly irradiated to the whole surface of the object of irradiation by combining small-sized low-energy electron accelerators with narrow irradiation windows and having the object of irradiation passed through an electron beam irradiation zone formed by these electron accelerators while a part of the object of irradiation is re-gripped and has completed the present invention.

That is, according to description in claim 1, the electron beam irradiation device according to the present invention has:

electron beam irradiation means (30) forming an electron beam irradiation zone (Z) by generating an electron beam; and gripping/moving means (40) gripping a part of an object of irradiation (P) and moving so that the object of irradiation passes through the electron beam irradiation zone, wherein the electron beam irradiation means is composed of three electron accelerators (31, 32, 33), each having an upper surface, a lower surface, and one side surface of the article of irradiation as irradiated surfaces, and is provided with three irradiation windows (31*a*, 32*a*, 33*a*) located substantially in parallel so as to face these three irradiated surfaces, respectively;

the irradiation window faced with the upper surface or the lower surface of the article of irradiation among the three irradiation windows has an irradiation width of at least ½ of the whole width of the upper surface or the lower surface of the object of irradiation, respectively, the irradiation window faced with the one side surface of the object of irradiation among the three irradiation windows has an irradiation width of at least the whole width of the one side surface of the object of irradiation;

the gripping/moving means is provided with two gripping mechanisms (45, 46) for gripping different portions of the object of irradiation, respectively, two moving mechanisms (41, 42) for moving the gripping mechanisms in a longitudinal direction, respectively, so that the objects of irradiation gripped by the two gripping mechanisms, respectively, pass through the electron beam irradiation zone, and two rotation mechanisms (43, 44) for rotating the gripping mechanisms so that the objects of irradiation gripped by the two gripping mechanisms, respectively are rotated; when the object of irradiation is gripped by the first gripping mechanism (45), by operations of the first moving mechanism (41) and the first rotation mechanism (43), a portion in the upper surface and the lower surface of the object of irradiation not including the portion gripped by the first gripping mechanism and a side surface among the side surfaces of the object of irradiation not including the portion gripped by the first gripping mechanism pass through the electron beam irradiation zone; and when the object of irradiation is spaced away from the first gripping mechanism and is gripped by the second gripping mechanism (46), by operations of the second moving mechanism (42) and the second rotation mechanism (44), a portion in the upper surface and the lower surface of the object of irradiation not including the portion gripped by the second gripping mechanism and a side surface among the side surfaces of the object of irradiation not including the portion gripped by the second gripping mechanism pass through the electron beam irradiation zone.

Moreover, according to description in claim 2, the present invention is the electron beam irradiation device described in claim 1, characterized in that the object of irradiation is a hexahedron composed of the upper surface, the lower surface, and the four side surfaces, provided with:

a first process of gripping the object of irradiation by the first gripping mechanism;

a second process in which at least ½ of the surface of each of the upper surface and the lower surface and the whole surface of the first side surface of the object of irradiation pass through the electron beam irradiation zone by movement of the first moving mechanism in one direction;

a third process in which the first rotation mechanism rotates the first gripping mechanism by 90° and the object of irradiation gripped by the first gripping mechanism is rotated by 90° in a horizontal direction;

a fourth process in which at least ½ of the surface of each of the upper surface and the lower surface and the whole surface of the second side surface of the object of irradiation pass through the electron beam irradiation zone by movement of the first moving mechanism in the opposite direction;

a fifth process of gripping the object of irradiation by the second gripping mechanism and of separating the same away from the first gripping mechanism;

a sixth process in which at least ½ of the surface of each of the upper surface and the lower surface and the whole surface of the third side surface of the object of irradiation pass through the electron beam irradiation zone by movement of the second moving mechanism in one direction;

a seventh process in which the second rotation mechanism rotates the second gripping mechanism by 90° and the object of irradiation gripped by the second gripping mechanism is rotated by 90° in the horizontal direction;

an eighth process in which at least ½ of the surface of each of the upper surface and the lower surface and the whole surface of the fourth side surface of the object of irradiation pass through the electron beam irradiation zone by movement of the second moving mechanism in the opposite direction; and a ninth process of separating the object of irradiation from the second gripping mechanism; and an operation is performed along the first to ninth processes when the whole surface of the object of irradiation is sterilized.

Moreover, according to description in claim 3, the present invention is the electron beam irradiation device described in claim 2, characterized in that in at least one process of the first to ninth processes, the gripped portion of the second gripping mechanism or each of the gripped portions of the first gripping mechanism and the second gripping mechanism passes through the electron beam irradiation zone.

Moreover, according to description in claim 4, the present invention is the electron beam irradiation device described in any one of claims 1 to 3, characterized in that the first gripping mechanism has position modifying means (60) for modifying a position of the object of irradiation to an appropriate position in order to grip the object of irradiation.

Moreover, according to description in claim 5, the present invention is the electron beam irradiation device described in any one of claims 1 to 4, comprising:

a carrying-in pass box (71) for carrying the object of irradiation into the electron beam irradiation device;

first conveying means (51) for conveying the unsterilized object of irradiation from outside the electron beam irradiation device to a gripping position of the first gripping mechanism through this carrying-in pass box;

a carrying-out pass box (72) for carrying the object of irradiation out to outside the electron beam irradiation device; and second conveying means (52) for conveying the sterilized object of irradiation from a gripping position of the second gripping mechanism to outside the electron beam irradiation device through this carrying-out pass box.

Moreover, according to description in claim 6, the present invention is the electron beam irradiation device described in claim 5, characterized in that the carrying-in pass box has a first carrying-in port (73) opened between an inside of the carrying-in pass box and an outside of the electron beam irradiation device and a second carrying-in port (25) opened between the inside of the carrying-in pass box and an inside of the electron beam irradiation device;

the carrying-out pass box has a first carrying-out port (26) opened between an inside of the carrying-out pass box and the inside of the electron beam irradiation device and a second carrying-out port (74) opened between an inside of the carrying-out pass box and the outside of the electron beam irradiation device;

the first carrying-in port, the second carrying-in port, the first carrying-out port, and the second carrying-out port are provided with opening/closing doors (73a, 25a, 26a, 74a), respectively; and the first carrying-in port, the second carrying-in port, the first carrying-out port, and the second carrying-out port are opened linearly with respect to a conveying direction of the object of irradiation with opening portions in parallel.

Advantageous Effect of Invention

According to the above described configuration, the electron beam irradiation device according to the present invention irradiates an electron beam from an upper side, a lower side, and one side of the object of irradiation. Moreover, an electron accelerator having an irradiation window narrower than the irradiated width of the upper surface and the lower surface of the object of irradiation can be employed, and by combining gripping, moving, and rotation of the object of irradiation by the gripping/moving means, the electron beam is irradiated to the whole surface in plural times. Since the electron beam is irradiated in plural times, the electron beam can be irradiated uniformly from a short distance to an irradiated surface. Moreover, since the electron beam can be irradiated from the short distance to the irradiated surface, the electron accelerator can be operated with a lowered acceleration voltage.

As described above, the electron beam irradiation device according to the present invention has the equal sterilization level for the whole surface of the object of irradiation, and reliability and safety of the sterilization effect can be maintained high. Moreover, since the compact small-sized low-energy electron accelerator having a narrow irradiation window can be employed, the electron beam irradiation device itself becomes compact, and the initial cost of the device including the cost of the electron accelerator can be kept low. Furthermore, since this small-sized low-energy electron accelerator can be operated with a low acceleration voltage, the usage limit (life) of the electron accelerator is extended, and the maintenance cost of the device can be kept low.

Moreover, according to the above described configuration, the electron beam irradiation device according to the present invention may be provided with the carrying-in pass box and the carrying-out pass box. As described above, by providing the two pass boxes before and after the electron beam irradiation device, the sterilized state inside the electron beam irradiation device is maintained, and leakage of X-rays generated in the electron beam irradiation device to the outside can be prevented.

Furthermore, the first carrying-in port and the second carrying-in port of the carrying-in pass box and the first carrying-out port and the second carrying-out port of the carrying-out pass box may be provided with the opening/closing doors, respectively. By controlling opening/closing of these opening/closing doors, the sterilized state in the electron beam irradiation device is further stably maintained, and leakage of the X-rays generated in the electron beam irradiation device to the outside can be completely prevented.

As described above, in the present invention, the electron beam irradiation device can be provided which can irradiate the electron beam uniformly to the entire outer surface of the object of irradiation by using the small-sized low-energy electron accelerator with a narrow irradiation window, can make the sterilization level of each portion substantially equal so as to maintain reliability and safety of the sterilization effect high, and can keep the initial cost and the maintenance cost of the device low by extending the cost and the usage limit (life) of the electron accelerator.

BRIEF DESCRIPTION OF DRAWINGS

FIG. 1 is a perspective view illustrating an object of irradiation (package) of an electron beam irradiation device according to this embodiment.

DESCRIPTION OF EMBODIMENTS

In the present invention, the term "sterilization" is assumed to be used in a broad meaning including a concept of "decontamination" other than the concept of the original "sterilization". Here, the original "sterilization" is, according to the "Guidance on the Manufacture of Sterile Pharmaceutical Products by Aseptic Processing" (so-called Japanese Aseptic Processing Guideline), defined as "a process that destroys or eliminates all types of microorganisms whether they are pathogens or non-pathogens which is to render a product free from microorganism".

On the other hand, the term "decontamination" is, according to the Japanese Aseptic Processing Guideline, defined as "a process that reduces or removes contaminating substances to a defined acceptance level using a reproducible method".

Here, since the number of germs cannot be made zero in terms of a probability concept, Sterility Assurance Level (SAL) is employed in practice. The original "sterilization" is assumed to destroy or eliminate all types of microorganisms from the outer packaged portion of an accommodating body and to guarantee the level of $SAL \leq 10^{-12}$. As a method which can guarantee this level, a method of setting a required dose in electron beam irradiation to 25 kGy (see ISO-13409), for example, can be used.

On the other hand, according to SAL, "decontamination" is assumed to reduce existing microorganisms from the outer packaged portion of the accommodating body and to guarantee the level of $SAL \leq 10^{-6}$. As a decontamination method which can guarantee this level, a method using hydrogen peroxide gas has been used. In the present invention, it can be handled by lowering the required dose in the electron beam irradiation to approximately 15 kGy, for example. Thus, as described above, in the present invention, the term "sterilization" is used in a wider concept including the original "sterilization" and "decontamination".

An embodiment of the electron beam irradiation device according to the present invention will be explained below by referring to the attached drawings. First, an object of irradiation of the electron beam irradiation device according to this embodiment will be explained. FIG. 1 is a perspective view illustrating a medical instrument package which is the object of irradiation in this embodiment. In FIG. 1, a package P is provided with a polyethylene tab P1 and an upper surface seal P2 made of Tyvek (registered trademark). In this embodiment, a large number of sterilized syringes to be used for a filling work of pre-filled syringes are accommodated therein and subjected to electron beam irradiation in the sealed state. In this embodiment, the package P having a size of 260 mm longitudinally, 230 mm horizontally, and 100 mm vertically is used.

Figure 2:
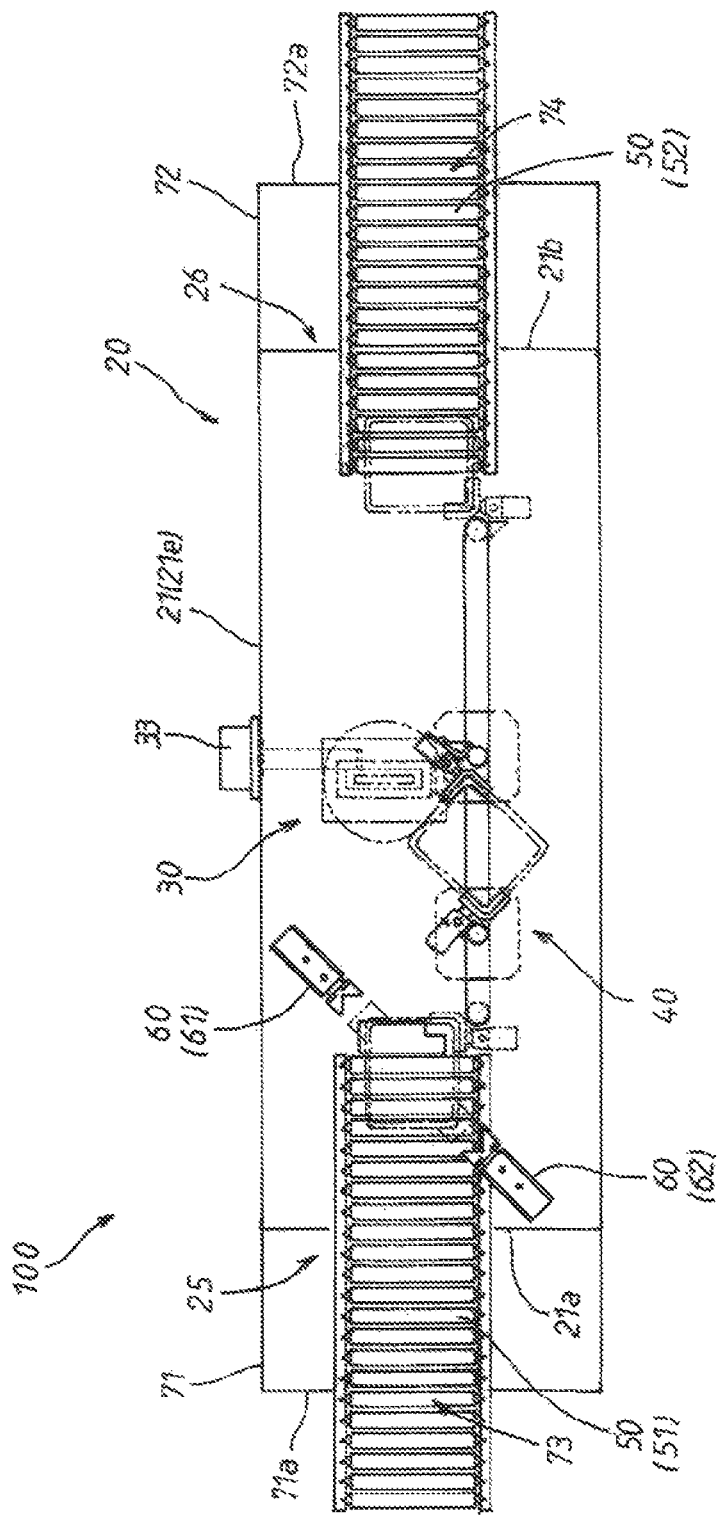
FIG. 2 is an outline plan view illustrating the electron beam irradiation device according to this embodiment.
Figure 3:
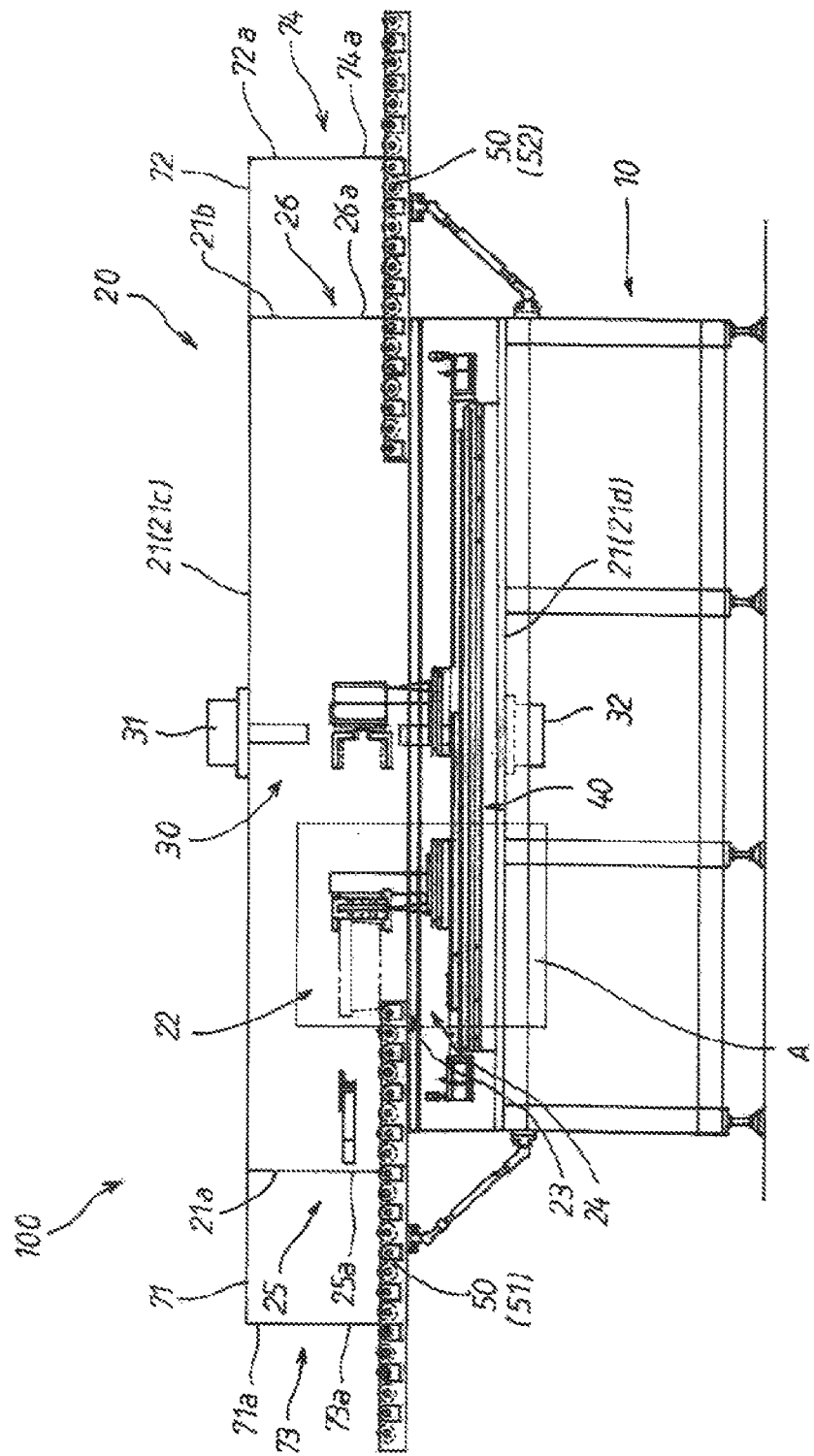
FIG. 3 is an outline front view illustrating the electron beam irradiation device in FIG. 2.

Subsequently, the electron beam irradiation device according to this embodiment will be explained. FIG. 2 is an outline plan view illustrating the electron beam irradiation device according to this embodiment, and FIG. 3 is an outline front view of the electron beam irradiation device. As illustrated in FIGS. 2 and 3, the electron beam irradiation device 100 according to this embodiment is composed of a body frame 10 placed on a floor surface, an electron beam irradiation device body 20 mounted on this body frame 10, and a carrying-in pass box 71 and a carrying-out pass box 72 provided continuously before and after this electron beam irradiation device body.

The electron beam irradiation device body 20 is covered by an outer wall portion 21 made of a stainless metal plate on the periphery, and an inside is divided into an electron beam irradiation chamber 22, a decompression chamber 23 located on its lower side, and a machine chamber 24 located on its further lower side by each of wall portions (see FIG. 4 which will be described later). The outer wall portion 21 shields the electron beam irradiated inside the electron beam irradiation chamber 22 and X-rays generated secondarily by this electron beam irradiation so that the X-rays do not leak to the outside.

In FIGS. 2 and 3, the carrying-in pass box 71 is provided continuously to the outer wall portion 21a on a left side surface of the electron beam irradiation device body 20. On an outer wall portion 71a on the left side surface of this carrying-in pass box 71, a first carrying-in port 73 through which the unsterilized package P is carried into the carrying-in pass box 71 is opened. On this first carrying-in port 73, a shutter 73a capable of being opened/closed in a vertical direction is provided.

Moreover, a wall portion faced with the outer wall portion 71a of the carrying-in pass box 71 constitutes a wall portion common with the outer wall portion 21a of the electron beam irradiation device body 20. On this wall portion, a second carrying-in port 25 having an inside of the electron beam irradiation chamber 22 and an inside of the carrying-in pass box 71 communicate with each other and through which the package P in the carrying-in pass box 71 is carried into the electron beam irradiation chamber 22 is opened. On this second carrying-in port 25, a shutter 25a capable of being opened/closed vertically is provided.

On the other hand, on an outer wall portion 21b on a right side surface of the electron beam irradiation device body 20, a carrying-out pass box 72 is continuously provided. A wall portion on a left side surface of this carrying-out pass box 72 constitutes a wall portion common with the outer wall portion 21b on the right side surface of the electron beam irradiation device body 20. On this wall portion, a first carrying-out port 26 having the inside of the electron beam irradiation chamber 22 and an inside of the carrying-out pass box 72 communicate with each other and through which the sterilized package P is carried out from the inside of the electron beam irradiation chamber 22 to the inside of the carrying-out pass box 72 is opened. On this first carrying-out port 26, a shutter 26a capable of being opened/closed vertically is provided.

Moreover, on an outer wall portion 72a on a right side surface of the carrying-out pass box 72 faced with the outer wall portion 21b on the right side surface of the electron beam irradiation device body 20, a second carrying-out port 74 through which the sterilized package P in the carrying-out pass box 72 is carried out from the electron beam irradiation device 100 is opened. On this second carrying-out port 74, a shutter 74a capable of being opened/closed vertically is provided. In this embodiment, this second carrying-out port 74 is opened toward an inside of an aseptic workroom (not shown) to which the electron beam irradiation device 100 is provided continuously, and the package P sterilized on the whole outer surface by the electron beam irradiation device 100 is carried into the aseptic work room.

Figure 4:
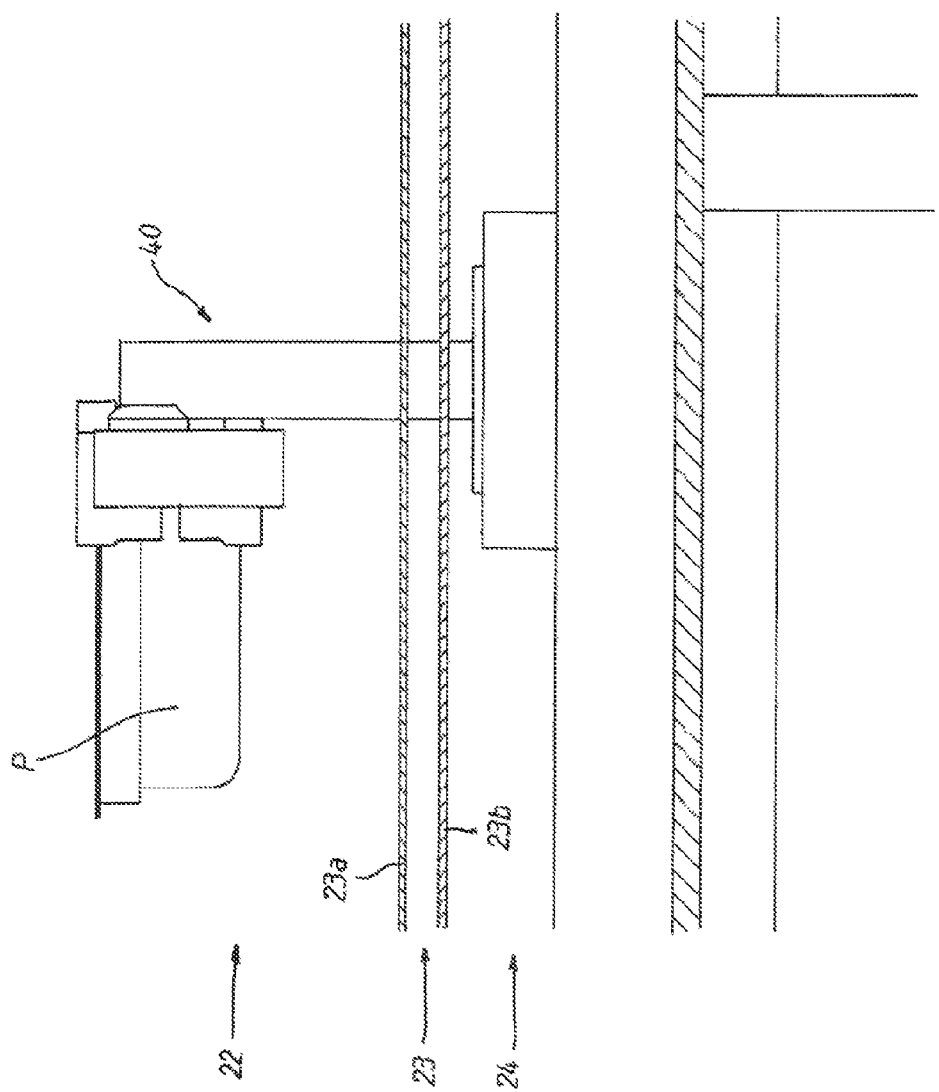
FIG. 4 is a partially enlarged view of A in FIG. 3.

FIG. 4 is a partially enlarged view of A in FIG. 3. In FIG. 4, the electron beam irradiation chamber 22 located on an upper layer portion is isolated from the decompression chamber 23 located on its lower side by a partition wall portion 23a, and in its inside, sterilization by the electron beam irradiation is performed while the package P is conveyed as will be described later. On the other hand, the machine chamber 24 located on a lower layer portion is isolated from the decompression chamber 23 located on its upper side by a partition wall portion 23b, and in its inside, a driving portion of a chuck-slide device (which will be described later) for conveying the package P is accommodated. The decompression chamber 23 located in a middle layer portion is isolated from the electron beam irradiation chamber 22 and the machine chamber 24 by the partition wall portion 23a and the partition wall portion 23b and is kept at a negative pressure with respect to the electron beam irradiation chamber 22 and the machine chamber 24 by an operation of a vacuum pump (not shown) provided outside. In order to keep the negative pressure, not only the vacuum pump but an air-discharge blower or the like may also be used.

Since the decompression chamber 23 is maintained at a negative pressure with respect to the electron beam irradiation chamber 22 and the machine chamber 24, ozone generated secondarily by electron beam irradiation is sucked to the outside from the electron beam irradiation chamber 22 through the decompression chamber 23, and corrosion inside the electron beam irradiation chamber 22 and the machine chamber 24 is alleviated. Moreover, since the quantity of ozone in the electron beam irradiation chamber 22 is decreased by the sucking, intrusion of ozone into the package P is drastically reduced, and an influence on end products such as the syringes accommodated therein and a filling liquid to be filled in the syringe in a subsequent process is made small. Moreover, since the decompression chamber 23 is maintained at the negative pressure with respect to the electron beam irradiation chamber 22 and the machine chamber 24, fine powder dusts by sliding and the like generated in the machine chamber 24 are sucked from the machine chamber 24 through the decompression chamber 23 to the outside, and the inside of the electron beam irradiation chamber 22, the package P, and the syringe accommodated therein are not contaminated.

Figure 5:
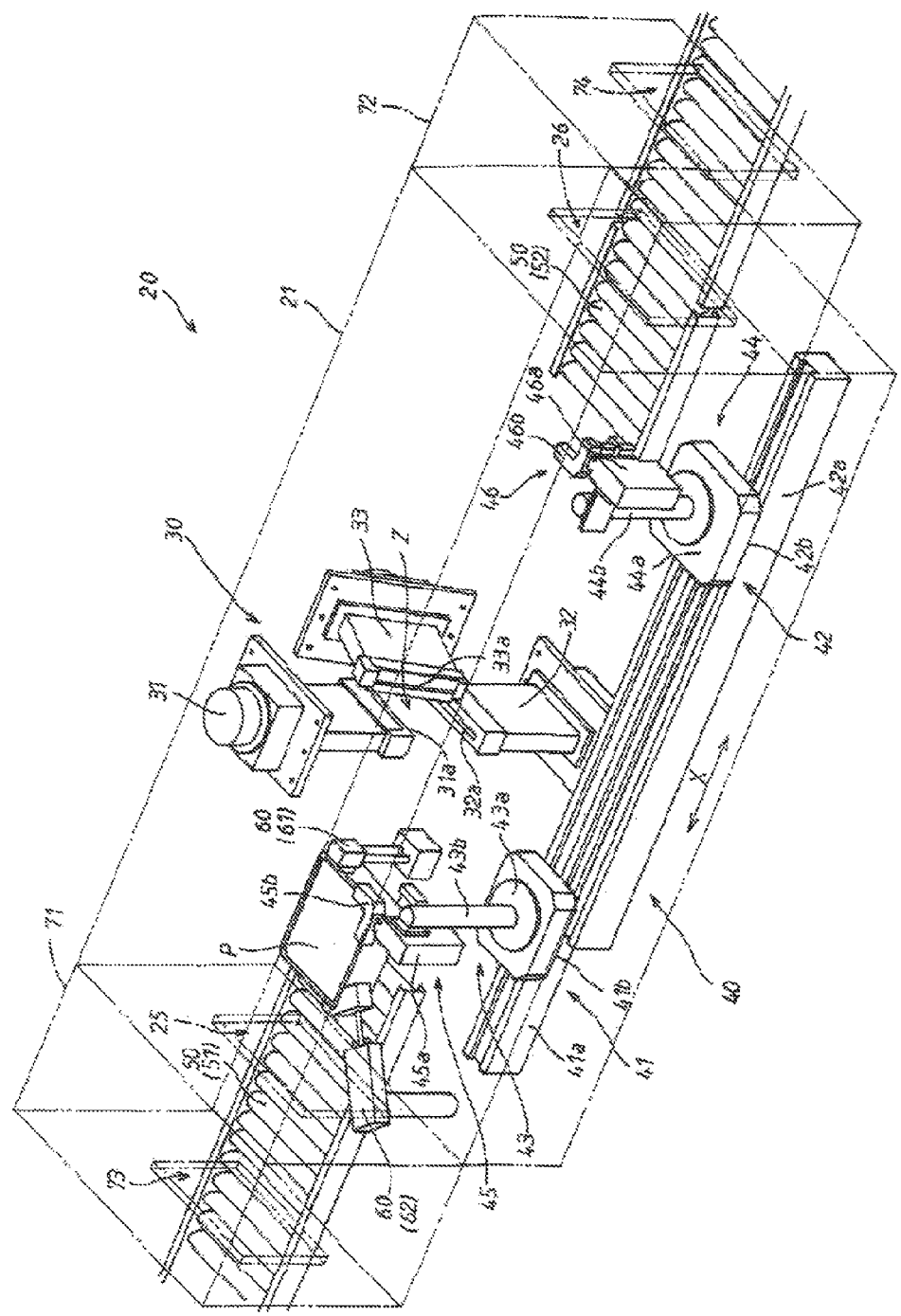
FIG. 5 is an outline perspective view illustrating an inside of a main body of the electron beam irradiation device in FIG. 3.

Here, the inside of the electron beam irradiation device according to this embodiment will be explained. FIG. 5 is an outline perspective view illustrating the inside of the electron beam irradiating device body 20. In FIG. 5, the outer wall portion 21 of the electron beam irradiation device body 20 and the outer wall portions of the carrying-in pass box 71 and the carrying-out pass box 72 are indicated by virtual lines, and the partition wall portion 23a and the partition wall portion 23b of the electron beam irradiation device body 20 are not shown. Moreover, in FIG. 5, the first carrying-in port 73 (the shutter 73a is not shown) and the second carrying-in port 25 (the shutter 25a is not shown) through which the unsterilized package P is carried into the electron beam irradiation chamber 22 are provided on an upper left side, and the first carrying-out port 26 (the shutter 26a is not shown) and the second carrying-out port 74 (the shutter 74a is not shown) through which the sterilized package P is carried out from the electron beam irradiation chamber 22 are provided on a lower right side. Therefore, in FIG. 5, the package P is conveyed from the upper left side to the lower right side. Hereinafter, this direction will be referred to as a conveying direction of the package P.

In FIG. 5, the electron beam irradiation device body 20 includes an electron beam generating device 30, a chuck-slide device 40, a conveying device 50, and a positioning cylinder 60 therein. The electron beam generating device 30 is disposed at a center part in the electron beam irradiation device body 20 and is composed of three electron accelerators 31, 32, and 33. The three electron accelerators 31, 32, and 33 have terminals generating the electron beam, acceleration tubes for accelerating the generated electron beam in a vacuum space, and power supply devices operate them (none of them is shown), respectively, and are provided with the irradiation windows 31a, 32a, and 33a irradiating the accelerated electron beam and made of metal foil. In this embodiment, each of the electron accelerators has an irradiation window narrower than a width of the upper surface or the lower surface of the package P and wider than a width of the side surface of the package P (width in the height direction). Specifically, a small-sized low-energy electron accelerator of the same type having the irradiation window with a long side (width direction) at 145 mm, a short side (length direction) at 25 mm with respect to the upper surface size (260 mm vertically) of the package P and with the acceleration voltage adjustable within a range of 40 to 70 kV is employed.

In FIG. 5, the electron accelerator 31 is provided with the irradiation window 31a irradiating the electron beam from the outer wall portion 21c (see FIG. 3) of the upper surface of the electron beam irradiation device body 20 faced downward inside the electron beam irradiation chamber 22. The electron accelerator 32 is provided with the irradiation window 32a irradiating the electron beam from the outer wall portion 21d (see FIG. 3) of the lower surface of the electron beam irradiation device body 20 faced upward inside the electron beam irradiation chamber 22. Moreover, the electron accelerator 33 is provided with the irradiation window 33a irradiating the electron beam from the outer wall portion 21e (see FIG. 2) of a rear surface of the electron beam irradiation device body 20 faced in a front surface direction and slightly upward inside the electron beam irradiation chamber 22. An irradiation direction of the electron accelerator 33 is provided not in a horizontal direction but in the slightly upward direction so as to be faced in parallel with the inclined side surface of the package P.

As described above, each of the electron accelerators 31, 32, and 33 is disposed from three directions so that the long side of each of the irradiation windows (width direction) is perpendicular to the conveying direction of the package P, and the electron beams irradiated from these three irradiation windows 31a, 32a, and 33a from an electron beam irradiation zone Z having a U-shape perpendicular to the conveying direction of the package P. A relationship between the electron beam irradiation zone Z formed by each of the irradiation windows 31a, 32a, and 33a and each of the surfaces of the package P will be described later.

Subsequently, the chuck-slide device 40 will be explained. In FIG. 5, the chuck-slide device 40 is disposed over a right-and-left direction (in parallel with the conveying direction of the package P) on a front side in the electron beam irradiation device body 20 and is provided with two linear-motor tables 41 and 42, two rotating members 43 and 44, and two chuck members 45 and 46. This chuck-slide device 40 makes the package P pass through the electron beam irradiation zone Z while conveying the same by conjunction of the two linear-motor tables 41 and 42, the two rotating members 43 and 44, and the two chuck members 45 and 46. Here, FIG. 6 is an outline perspective view illustrating the chuck-slide device 40 and unlike FIG. 5, illustrates a state in which a part of the partition wall portion 23a and the partition wall portion 23b isolating the electron beam irradiation chamber 22, the decompression chamber 23, and the machine chamber 24 from each other in the electron beam irradiation device body 20.

Figure 6:
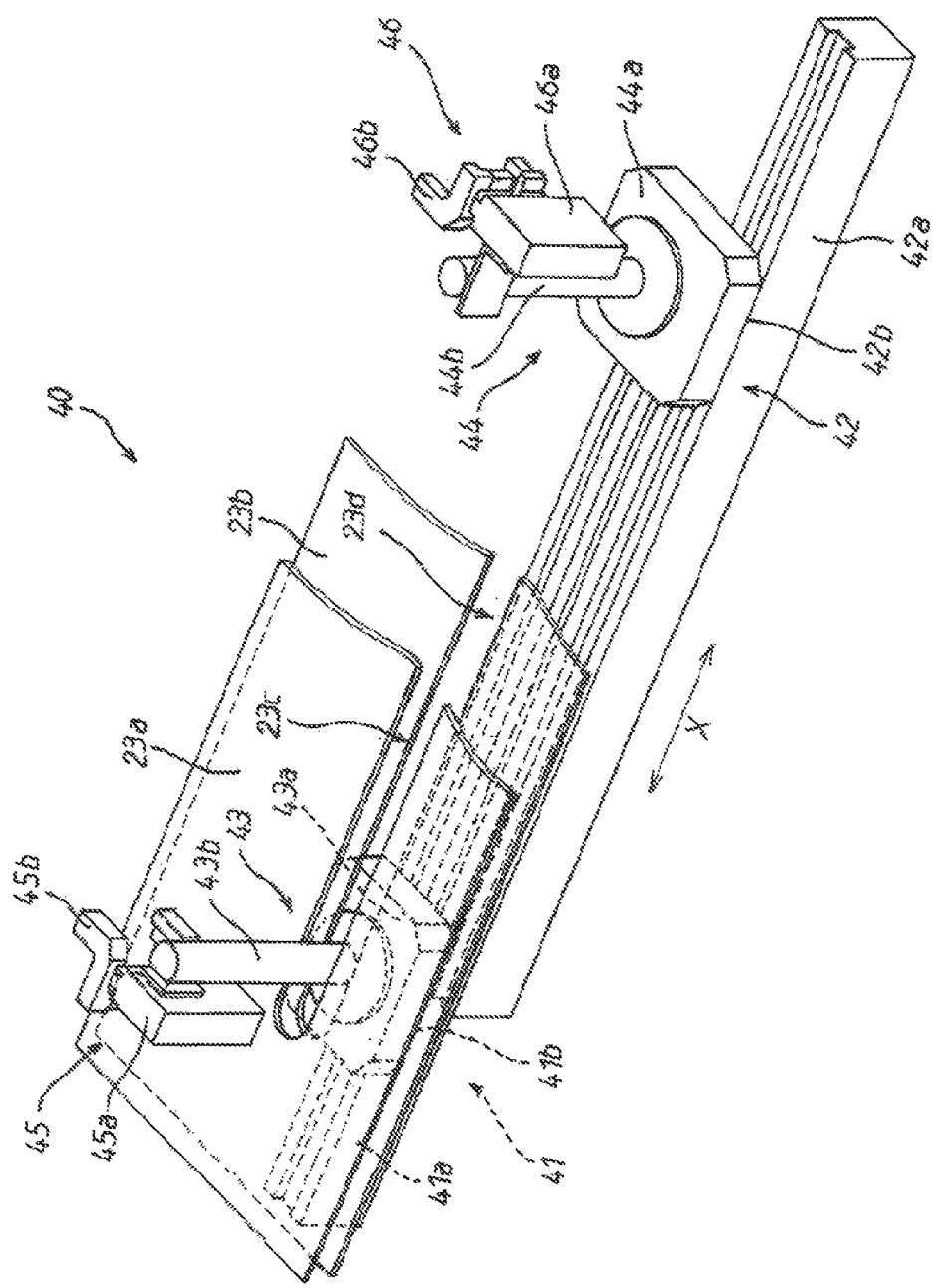
FIG. 6 is an outline perspective view illustrating a chuck-slide device in FIG. 5.

In FIGS. 5 and 6, the two linear-motor tables 41 and 42 are provided with two beds 41a and 42a disposed over the right-and-left direction (in parallel with the conveying direction of the package P) on the frontmost side of the electron accelerator 32 in the machine chamber 24 located on the lower layer portion of the electron beam irradiation device body 20, respectively, two movable tables 41b and 42b mounted on upper parts of the beds 41a and 42a, respectively, and two AC linear servo motors (not shown) incorporated between each of the beds 41a and 42a and each of the movable tables 41b and 42b.

In FIGS. 5 and 6, the two beds 41a and 42a are both elongated box bodies and are disposed in parallel with each other and in a perpendicular direction with respect to the U-shaped electron beam irradiation zone Z formed by the three electron accelerators 31, 32, and 33, respectively. The bed 41a is extended close to the left (the second carrying-in port 25 side) from a center part of the electron beam irradiation device body 20, while the bed 42a is extended close to the right (the first carrying-out port 26 side) from the center part of the electron beam irradiation device body 20. The two movable tables 41b and 42b are both regular-square plate bodies and reciprocate in the conveying direction of the package P on each of the beds 41a and 42a by an operation of each of the AC linear servo motors, respectively. In this embodiment, this reciprocation is referred to as movement in an X-axis direction.

Figure 7:
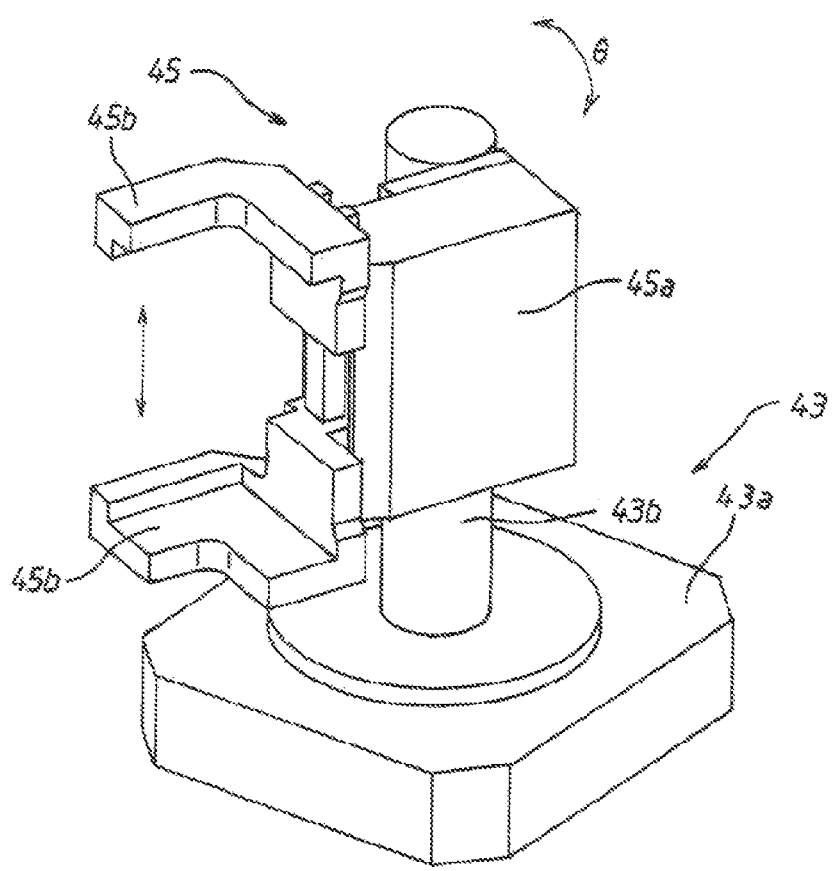
FIG. 7 is an outline perspective view illustrating a rotating member and a chuck member of the chuck-slide device.

Here, FIG. 7 is a perspective view illustrating the rotating member 43 and the chuck member 45 which are one of the two rotating members 43 and 44 and the two chuck members 45 and 46. In FIGS. 5, 6, and 7, the two rotating members 43 and 44 are provided with two rotation bases 43a and 44a mounted on the movable tables 41b and 42b, respectively, two rotation shafts 43b and 44b extending upward from the rotation bases 43a and 44a, respectively, and two rotation/driving motors (not shown) incorporated in the rotation bases 43a and 44a, respectively.

The two rotation bases 43a and 44a are both rectangular box bodies, are fixed to be integrated with the movable tables 41b and 42b, respectively, and reciprocate in the X-axis direction on the beds 41a and 42a together with the movable tables 41b and 42b by the operations of the linear-motor tables 41 and 42, respectively. The two rotation shafts 43b and 44b are both columnar bodies and extend in the vertical direction from the upper surfaces of the rotation bases 43a and 44a, respectively, and the extended end portions extend to the electron beam irradiation chamber 22 located on the upper layer portion of the electron beam irradiation device body 20 from the machine chamber 24 through the decompression chamber 23 above (see FIGS. 4 and 6). Each of the rotation shafts 43b and 44b rotates in either of counterclockwise and clockwise directions around its extending direction by driving of each of the rotation/driving motors. In this embodiment, this rotation will be referred to as rotation in a θ-axis direction.

In FIG. 6, the two rotation shafts 43b and 44b extend to the electron beam irradiation chamber 22 from the machine chamber 24 through laterally long slide opening portions 23c and 23d opened in parallel with the conveying direction of the package P in the two partition wall portions 23a and 23b isolating the electron beam irradiation chamber 22 and the machine chamber 24 from the decompression chamber 23, respectively. Thus, when the two rotating members 43 and 44 reciprocate in the x-axis direction on the beds 41a and 42a together with the movable tables 41b and 42b by the operations of the linear motor tables 41 and 42, respectively, the two rotation shafts 43b and 44b reciprocate in the X-axis direction along the slide opening portions 23c and 23d.

In FIGS. 5, 6, and 7, the two chuck members 45 and 46 are provided with two support portions 45a and 46a fixed to the rotation shafts 43b and 44b, respectively, two pairs of chuck claws 45b and 46b extending in the horizontal direction from the support portions 45a and 46a, respectively, and two opening/closing driving motors (not shown) incorporated in the support portions 45a and 46a, respectively.

The two support portions 45a and 46a are both rectangular box bodies, are fixed so as to extend in a tangent direction from outer peripheries of the extended end portions 43c and 44c of the rotation shafts 43b and 44b, respectively, and rotate in either of the outer peripheral directions with rotation of each of the rotation shafts 43b and 44b by the operation of each of the rotating members 43 and 44. The two chuck claws

45b and 46b are both composed of a pair of upper and lower claws each having an L-shape, and each extends in the horizontal direction from above and below the extended end portions 45c and 46c of the support portions 45a and 46a, respectively. These two chuck claws 45b and 46b are opened/closed in a vertical direction by driving of each of the opening/closing driving motor and grip a corner portion of the package P from the vertical direction (see FIG. 7). Arrangement of the two chuck claws 45b and 46b is symmetrical to each of the support portions 45a and 46a (see FIG. 6).

In FIG. 5, the conveying device 50 is composed of two driving-type roller conveyers 51 and 52 incorporating a driving motor. These two roller conveyers 51 and 52 may be both inclination type roller conveyers not incorporating the driving motor. Alternatively, they may be a combination of a horizontal non-driving type roller conveyer and a pusher.

The roller conveyer 51 is provided in the conveying direction of the package P toward the inside of the carrying-in pass box 71 and the electron beam irradiation chamber 22 from outside of the electron beam irradiation device 100 through the first carrying-in port 73 and the second carrying-in port 25 and conveys the unsterilized package P into the electron beam irradiation chamber 22 (see FIGS. 2 and 3). At this time, a guide for guiding conveyance of the package P may be provided on the roller conveyer 51. At a front end portion in an advancing direction of the roller conveyer 51 (in the electron beam irradiation chamber 22), the chuck member 45 receives the unsterilized package P (as will be described later).

The roller conveyer 52 is provided in the conveying direction of the package P toward the outside of the electron beam irradiation device 100 from insides of the electron beam irradiation chamber 22 and the carrying-out pass box 72 through the first carrying-out port 26 and the second carrying-out port 74 and carries out the sterilized package P to the outside of the electron beam irradiation device 100 (inside the aseptic work room) (see FIGS. 2 and 3). At this time, a guide for guiding conveyance of the package P may be provided on the roller conveyer 52. At a rear end portion in an advancing direction of the roller conveyer 52 (in the electron beam irradiation chamber 22), the chuck member 46 delivers the sterilized package P (as will be described later).

Figure 8:
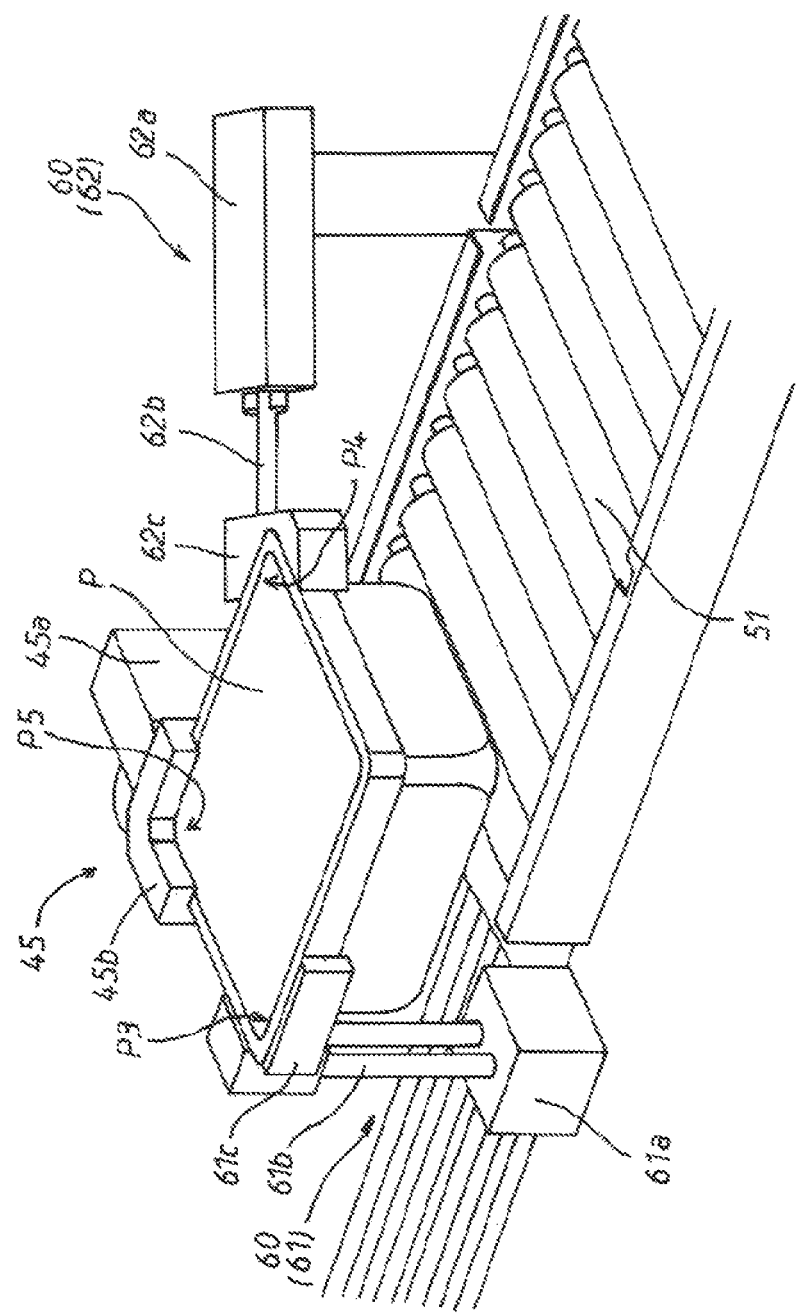
FIG. 8 is an outline perspective view illustrating arrangement of a positioning cylinder.

In FIG. 5, the positioning cylinder 60 is composed of two cylinders 61 and 62 provided on both right and left sides of the front end portion in the advancing direction of the roller conveyer 51 (in the electron beam irradiation chamber 22) and modifies the position of the unsterilized package P having been conveyed by the roller conveyer 51 to a position where the chuck member 45 can accurately grip the package P. Here, FIG. 8 is an outline perspective view illustrating arrangement of the positioning cylinder 60 and is a perspective view when seen from a diagonal line side (opposite side) of the package P with respect to FIG. 5. Therefore, in FIG. 8, the unsterilized package P is conveyed from the lower right side to the upper left direction.

In FIG. 8, the cylinder 61 is disposed on the left side on the front end portion in the advancing direction of the roller conveyer 51 and is provided with a rectangular base 61a provided on a bottom wall portion (partition wall 23a) of the electron beam irradiation chamber 22, a telescopic support 61b extending upward from an upper surface of the base 61a, an L-shaped fixed claw 61c fixed to an expanded end portion of the telescopic support 61b, and a telescopic driving motor (not shown) incorporated in the base 61a and expanding/contracting the telescopic support 61b.

The cylinder 62 is disposed on the diagonal line sandwiching the package P with the cylinder 61 on slightly on a rear right side from the front end portion in the advancing direction of the roller conveyer 51 and is provided with an L-shaped base 62a extending from the bottom wall portion (partition wall 23a) of the electron beam irradiation chamber 22 with its tip end extended in the direction of the cylinder 61, a telescopic support 62b extending horizontally from the tip end portion of the base 62a in the direction of the cylinder 61, an L-shaped fixed claw 62c fixed to an expanded end portion of the telescopic support 62b, and a telescopic driving motor (not shown) incorporated in the base 62a and expanding/contracting the telescopic support 62b. The two fixed claws 61c and 62c both grip two corner portions on the diagonal line of the package P in a state in which L-shaped inner surfaces are faced with each other.

An operation of sterilizing the outer packaged portion of the package P by using the electron beam irradiation device 100 according to this embodiment configured as above and of carrying this sterilized package P into the aseptic work room will be explained. In FIG. 3, the aseptic work room (not shown) is provided continuously to the outer wall portion 72a on the right side surface of the carrying-out pass box 72 of the electron beam irradiation device 100, and the filling work of the pre-filled syringe is performed inside this aseptic work room. At this time, the shutter 73a of the first carrying-in port 73, the shutter 25a of the second carrying-in port 25, the shutter 26a of the first carrying-out port 26, and the shutter 74a of the second carrying-out port 74 of the electron beam irradiation device 100 are all closed, and an external environment, the inside of the electron beam irradiation device 100, and the inside of the aseptic work room are shut off in an air-tight manner. The inside of the electron beam irradiation device 100 is sterilized by the hydrogen peroxide gas in advance to the level guaranteeing $SAL \leq 10^{-6}$.

Here, a worker in the external environment opens the shutter 73a of the first carrying-in port 73 opened in the carrying-in pass box 71 of the electron beam irradiation device 100 and carries the package P into the carrying-in pass box 71 through the roller conveyer 51 of the electron beam irradiation device 100. After that, the shutter 73a is closed. The package P having been carried into the carrying-in pass box 71 is conveyed into the electron beam irradiation chamber 22 through the shutter 25a of the second carrying-in port 25 while being conveyed by the roller conveyer 51. A series of operation processes from the operation of carrying the package P into the electron beam irradiation device 100 through the roller conveyer 51 to the operation of carrying the package P out of the electron beam irradiation device 100 through the roller conveyer 52 may be performed by a manual operation, respectively, or may be controlled by a control mechanism incorporating a microcomputer.

In FIG. 8, when the roller conveyer 51 is conveying the package P, the cylinder 61 of the positioning cylinder 60 expands the telescopic support 61b, and the fixed claw 61c stops at a fixed position. This position of the fixed claw 61c of the cylinder 61 corresponds to a corner portion P3 on front left in the conveying direction of the package P. In this state, the unsterilized package P having been conveyed from the lower right side in FIG. 8 stops at the front end portion in the advancing direction of the roller conveyer 51. This position of the package P is disturbed by conveyance, and the corner portion P3 on the front left in the conveying direction of the package P does not accurately correspond to the L-shaped position of the fixed claw 61c of the cylinder 61.

Therefore, it is difficult for the chuck member 45 to correctly grip the package P in this state. Thus, the telescopic support 62b of the cylinder 62 expands, while the fixed claw 62c is pushing a corner portion P4 on the diagonal line of the package P, and stops at the fixed position. In this state, the package P is stopped in a state gripped by the L-shaped fixed claws 61c and 62c of the cylinders 61 and 62 at the two corner portions P3 and P4 on the diagonal line and modified to the fixed position (see FIG. 8).

Subsequently, the chuck member 45 goes backward (moves to the rear in the conveying direction of the package P) in the X-axis direction on the bed 41a by the operation of the linear-motor table 41 and moves to the front end portion in the advancing direction of the roller conveyer 51. At this position, the chuck member 45 grips another corner portion P5 of the package P from the vertical direction and grasps it. Subsequently, the telescopic support 61b of the cylinder 61 retracts downward, and the telescopic support 62b of the cylinder 62 retracts rearward. From this state, the chuck member 45 advances in the conveying direction (upper left direction in FIG. 8, lower right direction in FIG. 5) of the package P while gripping the package P. Subsequently, in FIG. 5, the package P passes through the electron beam irradiation zone Z while being gripped by the chuck member 45 which advances (moves to the front in the conveying direction of package P) in the X-axis direction on the bed 41a by the operation of the linear-motor table 41.

Figure 9:
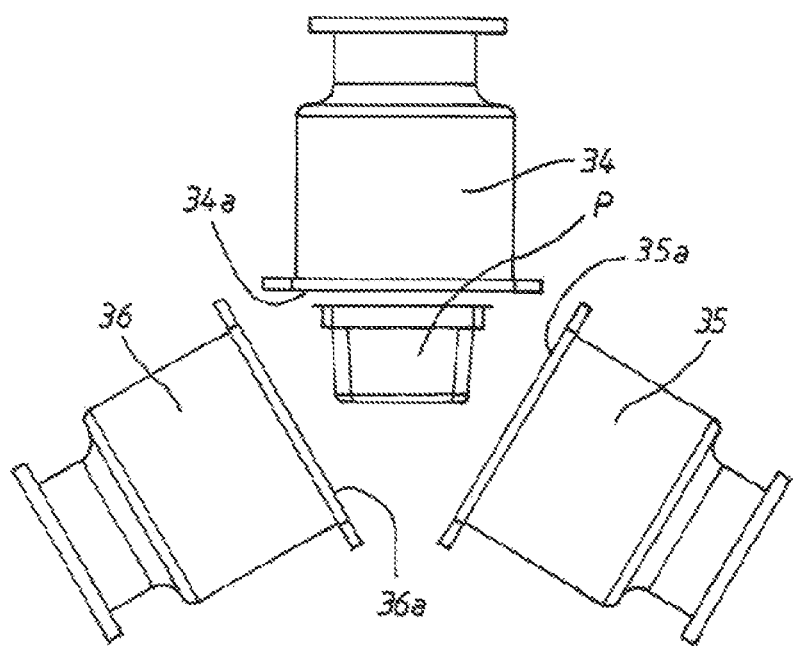
FIG. 9 is an outline view illustrating arrangement of electron accelerators of a prior-art electron beam irradiation device.

Here, a relationship between arrangement of the three electron accelerators 31, 32, and 33 in the electron beam irradiation device 100 according to this embodiment and each of the surfaces of the package P will be explained in comparison with the arrangement of the electron accelerators in the prior-art electron beam irradiation device. FIG. 9 is an outline view illustrating the arrangement of the electron accelerators of the prior-art electron beam irradiation device. In FIG. 9, three low-energy electron accelerators 34, 35, and 36 arranged by an angle of 120 degrees from each other irradiate the electron beam to the whole surface of the package P from three directions. Moreover, the package P moves toward a front surface direction from a rear surface direction in the figure and can irradiate the electron beam to the whole surface including the front and rear surfaces of the package P.

Thus, in the prior-art electron beam irradiation device, as illustrated in FIG. 9, the electron accelerators with large irradiation windows 34a, 35a, and 36a should be used. Moreover, a distance from each of the irradiation windows 34a, 35a, and 36a of the electron accelerators to each of irradiated portions of the package P is different from each other, and uniform electron beam irradiation cannot be performed, and in order to realize stable sterilization, a higher acceleration voltage is needed. For example, the irradiation window of the prior-art electron accelerator is large laterally and vertically at 400 mm, and the acceleration voltage is as high as 150 to 300 kV. Thus, the cost of the electron accelerator is high, the initial cost of the device rises, and operation with raised acceleration voltage shortens a usage limit (life) of the electron accelerator and raises the maintenance cost.

Figure 10:
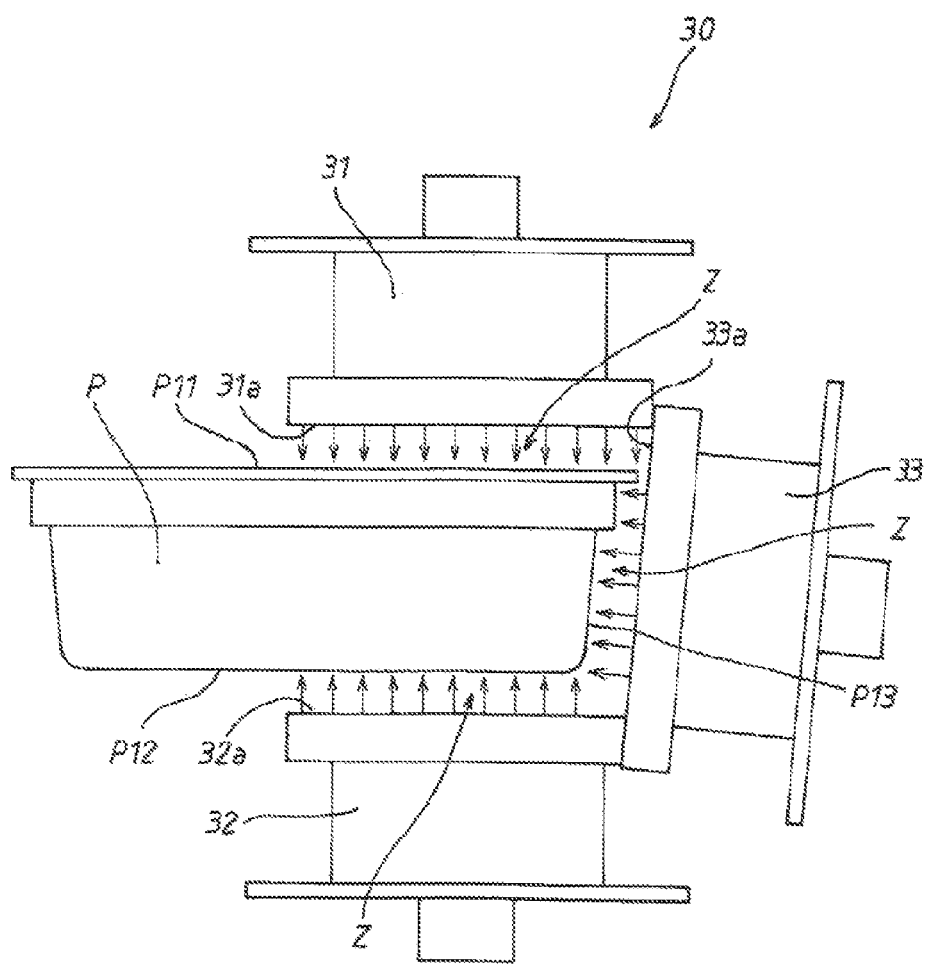
FIG. 10 is an outline view illustrating arrangement of electron accelerators of the electron beam irradiation device according to this embodiment.

On the other hand, FIG. 10 is an outline view illustrating the arrangement of the electron accelerators of the electron beam irradiation device according to this embodiment. In FIG. 10, the electron beam irradiation device 100 according to this embodiment is, as described above, provided with the three electron accelerators 31, 32, and 33. The electron accelerator 31 is located with the long side (width direction) of its irradiation window 31a faced in parallel with a surface of approximately ½ of an upper surface P11 of the package P. The electron accelerator 32 is located with the long side (width direction) of its irradiation window 32a faced in parallel with a surface of approximately ½ of a lower surface P12 of the package P. The electron accelerator 33 is located with the long side (width direction) of its irradiation window 33a faced in parallel with the whole surface of one side surface P13 of the package P. In FIG. 10, though not shown, the package P moves from the rear surface direction to the front surface direction of the figure or in the opposite direction in a state in which the illustrated left-side corner portion is gripped by the chuck member 45 or 46.

As described above, the three electron accelerators 31, 32, and 33 of the electron beam irradiation device 100 according to this embodiment irradiate electron beams from the upper side, the lower side, and one of sides of the package P. In FIG. 10, since the three electron accelerators 31, 32, and 33 irradiate the electron beams substantially in the perpendicular direction from each of the irradiation windows, a U-shaped zone surrounded by them is the electron beam irradiation zone Z. In this embodiment, each of the irradiation windows 31a, 32a, and 33a of the electron accelerators has a small irradiation width of a half or less of that of the prior-art electron accelerator in FIG. 9, and the electron accelerators 31, 32, and 33 themselves may be also compact. Moreover, as will be described later, since a portion with a long distance from the irradiation window is sterilized in another process, the front and rear surfaces do not have to be sterilized. Therefore, the width of the irradiation window may also be small. In this embodiment, the electron accelerator having the irradiation window with the long side (width direction) of 145 mm and the short side (length direction) of 25 mm as described above is employed. As a result, the cost of the electron accelerator is low, and the initial cost of the device can be kept low.

Moreover, the irradiation windows 31a, 32a, and 33a of the electron accelerators and the upper surface P11, the lower surface P12, and one side surface P13 which are irradiated portions of the package P are faced with each other substantially in parallel. Moreover, the distances among them are substantially equal, and uniform electron beam irradiation can be made from a short distance. As a result, the acceleration voltage of each of the electron accelerators can be kept low, the usage limit (life) of the electron accelerator is extended, and the maintenance cost of the device can be kept low. In this embodiment, the distance from each of the irradiation windows to the package P is set to approximately 20 mm, and the acceleration voltage is operated at 70 kV.

In this embodiment, as illustrated in FIG. 10, the surface of approximately ½ of the upper surface P11 and the surface of approximately ½ of the lower surface P12 of the package P to which the electron beam is irradiated are on the same side (right side in FIG. 10) as the side surface P13, and these surfaces pass through the electron beam irradiation zone Z and sterilized. On the other hand, the remaining surfaces of the upper surface P3 and the lower surface P4 (left side in FIG. 10) and the three side surfaces other than the side surface P5 (the left side surface and the front and rear surfaces in FIG. 10) of the package P are scarcely subjected to electron beam irradiation or sterilized. However, in this embodiment, the whole surface of the package P can be sterilized by electron beam irradiation by the operation of the chuck-slide device 40.

The method of sterilization of the whole surface of the package P will be explained below by using FIGS. 11 to 20 along a first process to a ninth process illustrating the operation of the chuck-slide device 40. FIGS. 11 to 20 all illustrate a positional relationship between movement of the two chuck members 45 and 46 and the package P with respect to the electron beam irradiation zone Z.

Figure 11:
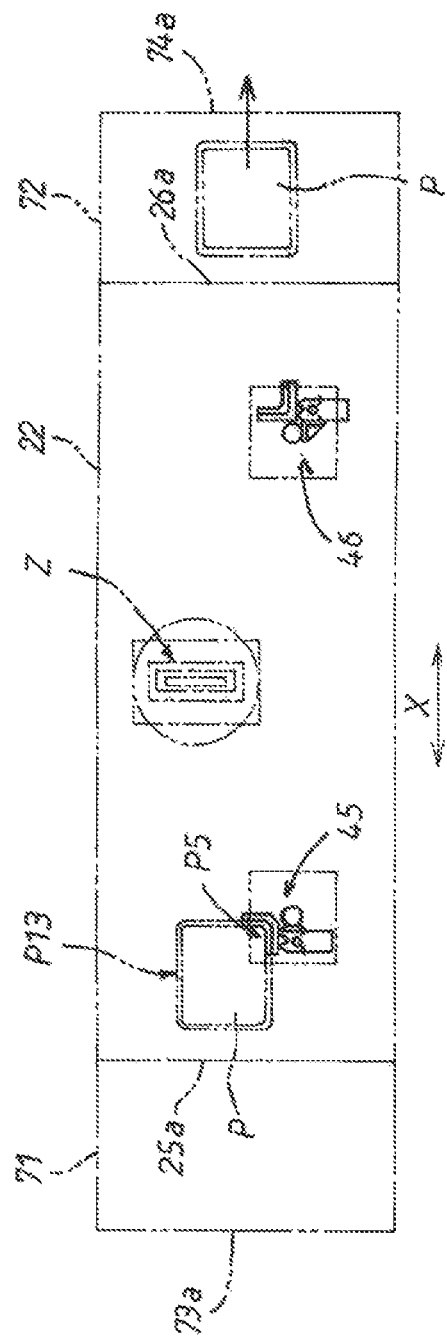
FIG. 11 is a process diagram 1 illustrating an operation of the chuck-slide device.

(First process) In the first process, in FIG. 11, the package P having been conveyed by the operation of the roller conveyer 51 through the two shutters 73a and 25a of the carrying-in pass box 71 is fixed at the fixed position by the operation of the positioning cylinder 60 (not shown) as described above, and with the backward movement in the X-axis direction (movement to the rear in the conveying direction of the package P) of the movable table 41b by the operation of the linear-motor table 41, the chuck member 45 moves to a predetermined position. At this position, the package P is gripped at the corner portion P5 by the chuck 45b of the chuck member 45 (see FIG. 8). The subsequent operation of the cylinder 60 has been described above.

At this time, on the front in the conveying direction (right side in FIG. 11) of the package P, the package P having been already sterilized is carried out to the outside of the electron beam irradiation device 100 (into the aseptic work room) through the two shutters 26a and 74a of the carrying-out pass box 72 by the operation of the roller conveyer 52.

Figure 12:
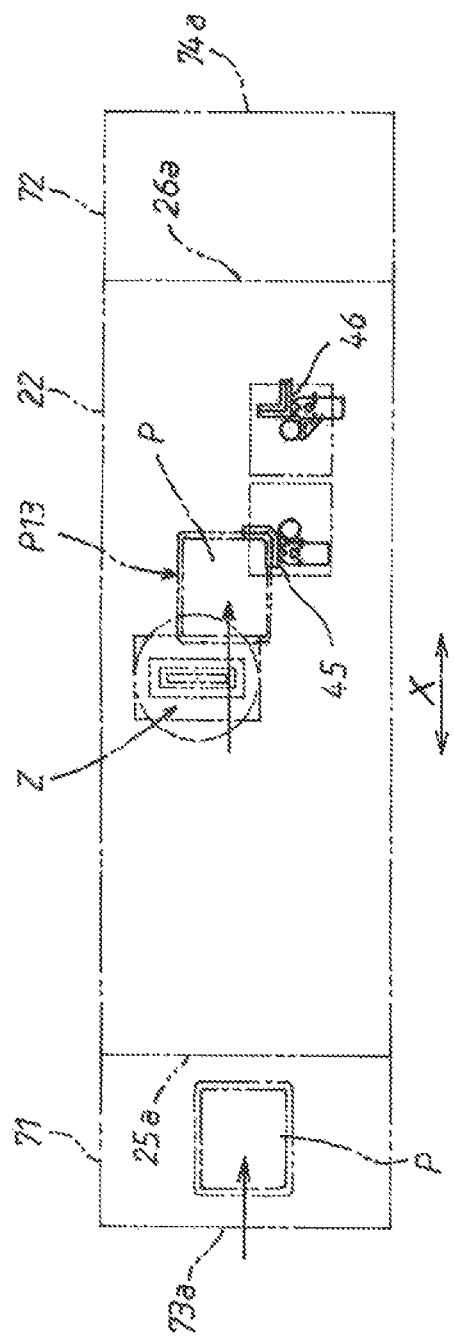
FIG. 12 is a process diagram 2 illustrating the operation of the chuck-slide device.

(Second process) In the second process, in FIG. 12, in the state in which the package P is gripped at the corner portion P5 by the chuck member 45, with forward movement in the X-axis direction (movement to the front in the conveying direction of the package P) of the movable table 41b by the operation of the linear-motor table 41, at least ½ of the surface of each of the upper surface P11 and the lower surface P12 of the package P (half on the upper side in illustration) and the whole surface of the side surface P13 pass the electron beam irradiation zone Z. In this second process, at least ½ of the surface of each of the upper surface P11 and the lower surface P12 of the package P and the whole surface of the side surface P13 are sterilized.

At this time, in the rear in the conveying direction (left side in FIG. 12) of the package P, another package P to be sterilized next is carried into the carrying-in pass box 71 through the shutter 73a by the operation of the roller conveyer 51 and stands by.

Figure 13:
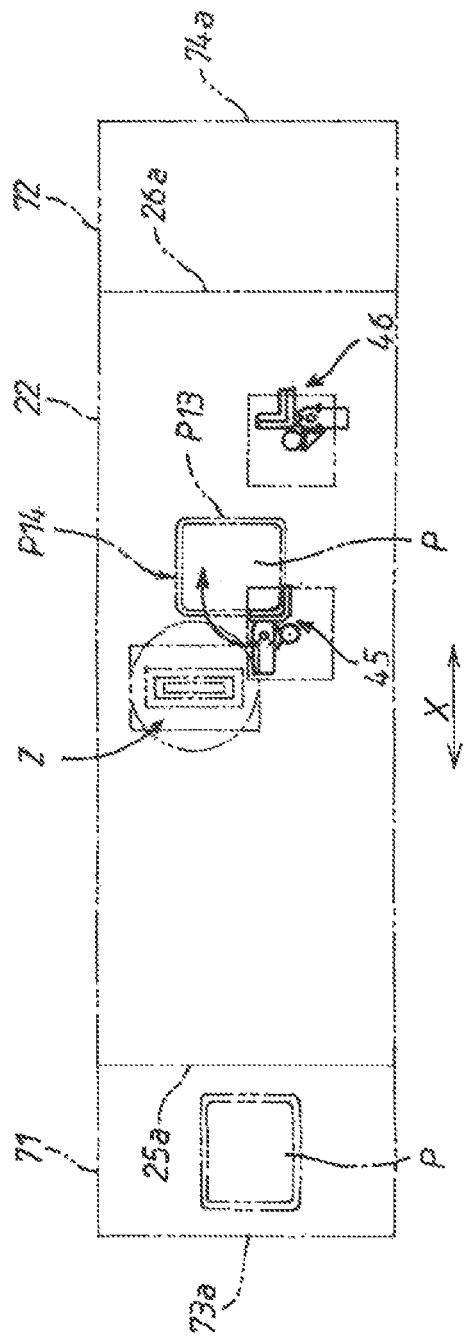
FIG. 13 is a process diagram 3 illustrating the operation of the chuck-slide device.

(Third process) In the third process, in FIG. 13, in the state in which the package P is gripped at the corner portion P5 by the chuck member 45, the rotating member 43 rotates the rotation shaft 43b forward in the θ-axis direction (clockwise) by 90° and rotates the package P gripped by the chuck member 45 in the horizontal direction by 90° around the rotation shaft 43b. As a result, a side surface P14 adjacent to the side surface P13 of the package P can pass through the electron beam irradiation zone Z.

Figure 14:
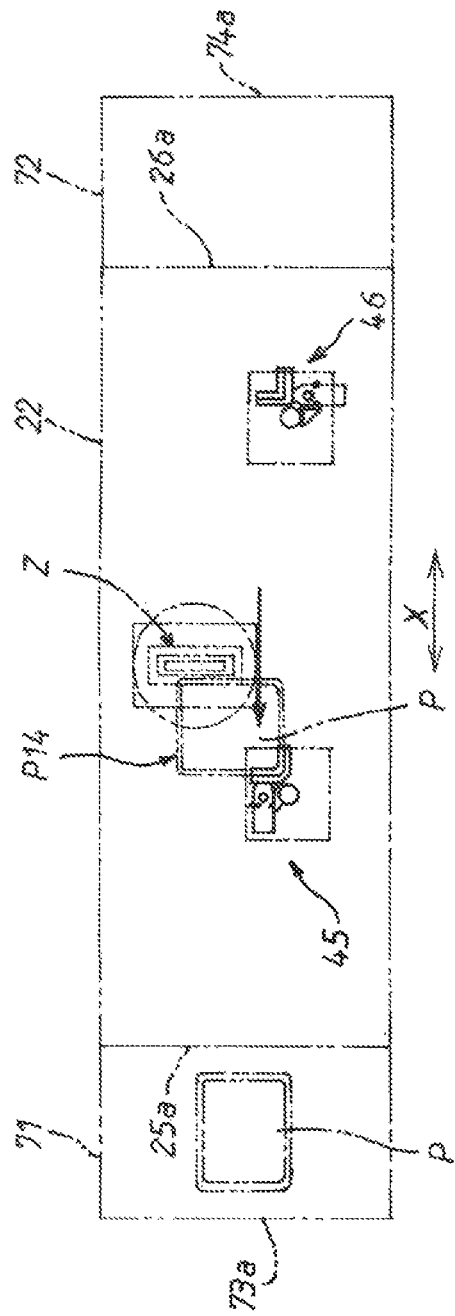
FIG. 14 is a process diagram 4 illustrating the operation of the chuck-slide device.

(Fourth process) In the fourth process, in FIG. 14, in the state in which the package P is gripped at the corner portion P5 by the chuck member 45, with backward movement in the X-axis direction (movement to the rear in the conveying direction of the package P) of the movable table 41b by the operation of the linear-motor table 41, at least ½ of the surface of each of the upper surface P11 and the lower surface P12 (half on the upper side in illustration) and the whole surface of the side surface P14 of the package P pass through the electron beam irradiation zone Z. In this fourth process, at least ½ of the surface of each of the upper surface P11 and the lower surface P12 and the whole surface of the side surface P14 of the package P are sterilized.

Therefore, by using the second process and the fourth process at the same time, at least ¾ of the surface of each of the upper surface P11 and the lower surface P12 and the whole surface of the side surface P13 and the side surface P14 (½ of the whole side surfaces) of the package P are sterilized. Here, at least ¼ of the surfaces of the upper surface P11 and the lower surface P12 of the package P on the diagonal line with the chuck member 45, respectively, passes through the electron beam irradiation zone Z from a short distance twice in the second process and the fourth process.

Figure 15:
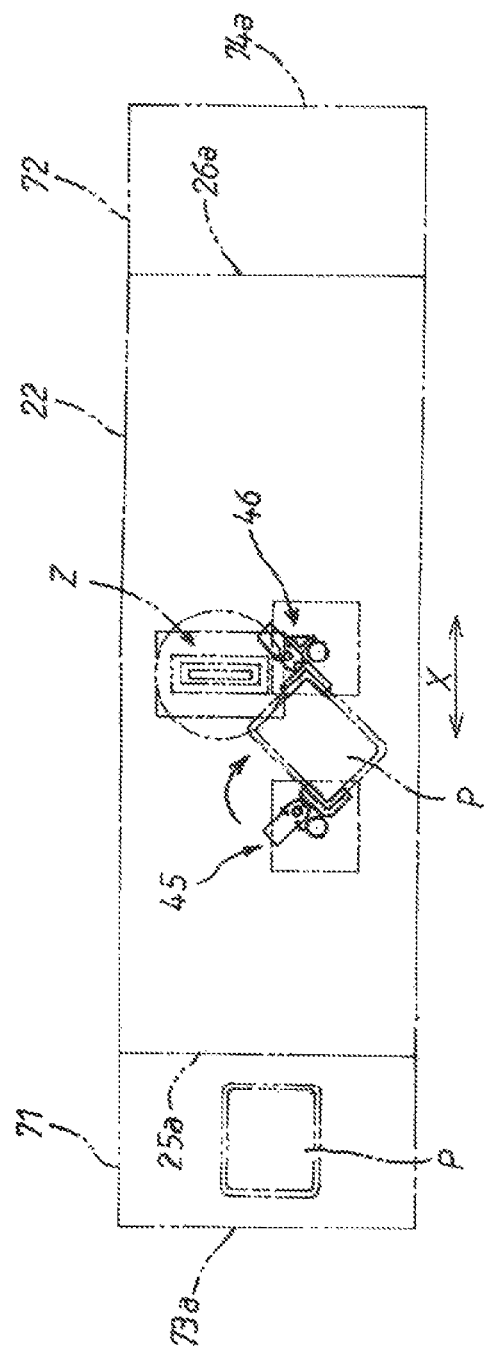
FIG. 15 is a process diagram 5 illustrating the operation of the chuck-slide device.
Figure 16:
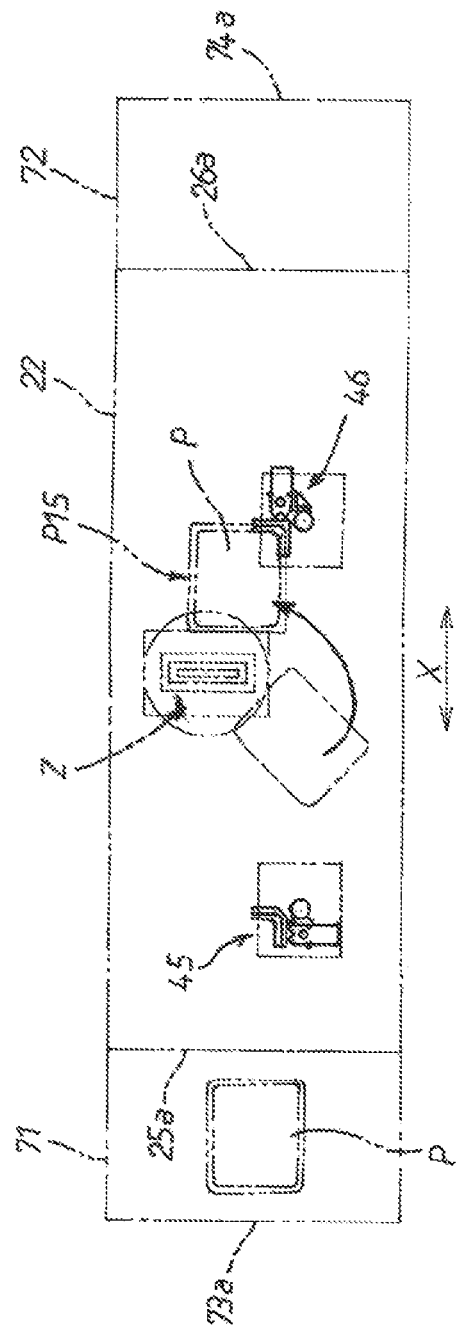
FIG. 16 is a process diagram 6 illustrating the operation of the chuck-slide device.

(Fifth process) In the fifth process, in FIGS. 15 and 16, the package P is delivered from the gripped state by the chuck member 45 to a state gripped by the chuck member 46. Specifically, first, in FIG. 15, in the state in which the package P is gripped by the chuck 45 at the corner portion P5, the rotating member 43 rotates the rotation shaft 43b forward in the θ-axis direction (clockwise) by 45°. Subsequently, with the backward movement in the X-axis direction (movement to the rear in the conveying direction of the package P) of the movable table 42b by the operation of the linear-motor table 42, the chuck member 46 is moved to the predetermined position. At this position, the package P is gripped by the chuck 46b of the chuck member 46 at a corner portion P6.

At this point of time, the package P is gripped by the two chuck members 45 and 46 at the two corner portions P5 and P6 on the diagonal line. Subsequently, when the chuck 45b of the chuck member 45 releases the corner portion P6, the package P enters the state gripped singularly by the chuck member 46 at the corner portion P6. Here, the chuck 46b of the chuck member 46 is sterilized by the hydrogen peroxide gas in advance to the level guaranteeing SAL≤$10^{-6}$ as described above.

Subsequently, in FIG. 16, in the state in which the package P is gripped by the chuck member 46 at the corner portion P6, the rotating member 44 rotates the rotation shaft 44b backward in the θ-axis direction (counterclockwise) by a predetermined angle so that, even if the package P moves, it does not pass through the electron beam irradiation zone Z. In this state, with the forward movement in the X-axis direction (movement to the front in the conveying direction of the package P) of the movable table 42b by the operation of the linear-motor table 42, the package P moves to the position on the right side (front in the conveying direction of the package P) of the electron beam irradiation zone Z in the state in which the corner portion P6 is gripped by the chuck member 46. During this movement, the package P does to pass through the electron beam irradiation zone Z. The reason why this operation is added is to irradiate the electron beam uniformly to the whole surface of the package P in the four processes in which the package P passes through the irradiation zone. That is, if the package P passes through the irradiation zone other than the above four processes, a part of the surface of the package P is irradiated in excess, and the whole surface cannot be irradiated uniformly. Moreover, as a result, the package P after sterilization of the whole surface has been completed can be located on the carrying-out pass box 72 side on the front in the conveying direction (right side in FIG. 16).

Subsequently, in the state in which the package P is gripped by the chuck member 46 at the corner portion P6, the rotating member 44 rotates the rotation shaft 44b forward in the θ-axis direction (clockwise) by a predetermined angle and rotates the package P gripped by the chuck member 46 in the horizontal direction around the rotation shaft 44b. As a result, a side surface P15 adjacent to the side surface P14 of the package P comes to the position capable of passing through the electron beam irradiation zone Z.

Figure 17:
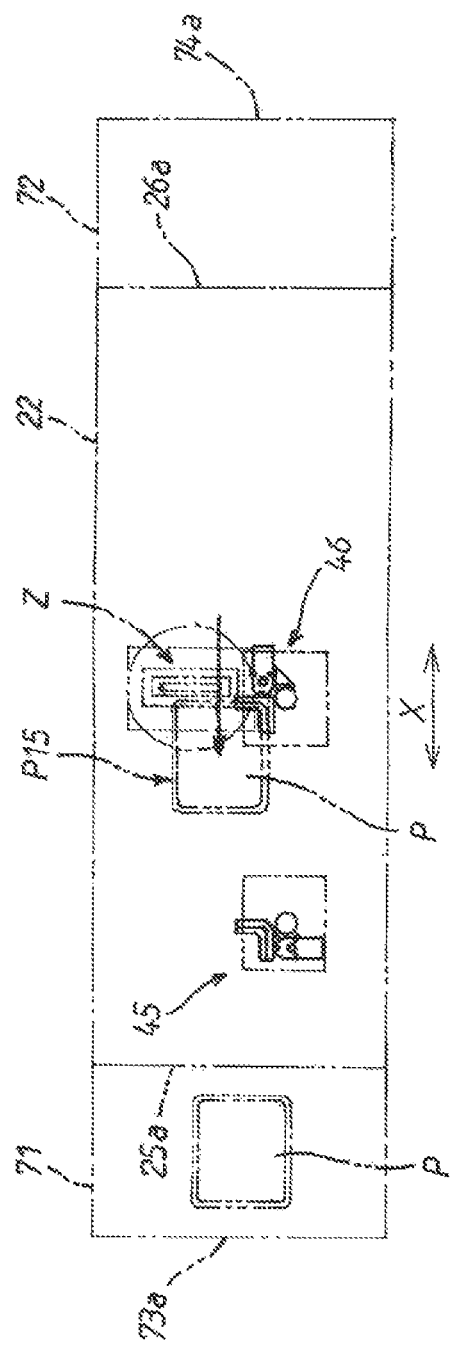
FIG. 17 is a process diagram 7 illustrating the operation of the chuck-slide device.

(Sixth process) In the sixth process, in FIG. 17, in the state the package P is gripped by the chuck member 46 at the corner portion P6, with the backward movement in the X-axis direction (movement to the rear in the conveying direction of the package P) of the movable table 42b by the operation of the linear-motor table 42, at least ½ of the surface of each of the upper surface P11 and the lower surface P12 (half on the upper side in illustration) and the whole surface of the side surface P15 of the package P pass through the electron beam irradiation zone Z In this sixth process, at least ½ of the surface of each of the upper surface P11 and the lower surface P12 of the package P and the whole surface of the side surface P15 are sterilized.

Therefore, by using the second process, the fourth process, and the sixth process at the same time, the whole surface of each of the upper surface P11 and the lower surface P12 and the whole surfaces of the side surface P13, the side surface P14, and the side surface P15 of the package P (¾ of the whole surface) are sterilized. Here, at least ½ of the surface of each of the upper surface P11 and the lower surface P12 of the package P passes through the electron beam irradiation zone Z from the short distance twice.

Figure 18:
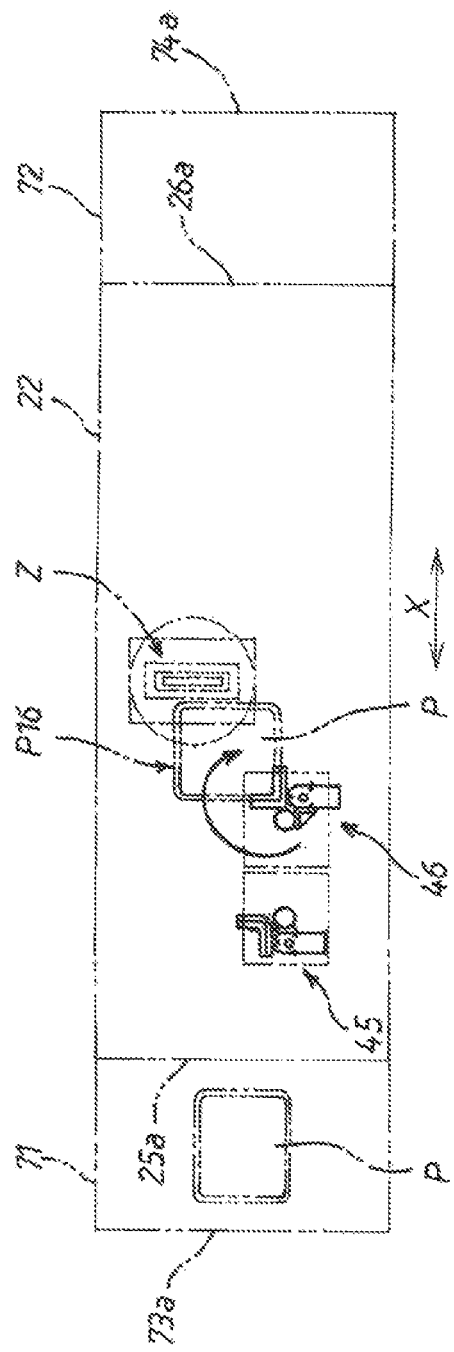
FIG. 18 is a process diagram 8 illustrating the operation of the chuck-slide device.

(Seventh process) In the seventh process, in FIG. 18, in the state in which the package P is gripped by the chuck member 46 at the corner portion P6, the rotating member 44 rotates the rotation shaft 44b forward in the θ-axis direction (clockwise) by 90° and rotates the package P gripped by the chuck member 46 in the horizontal direction around the rotation shaft 44b by 90°. As a result, a side surface P16 adjacent to the side surface P15 of the package P comes to the position capable of passing through the electron beam irradiation zone Z.

Figure 19:
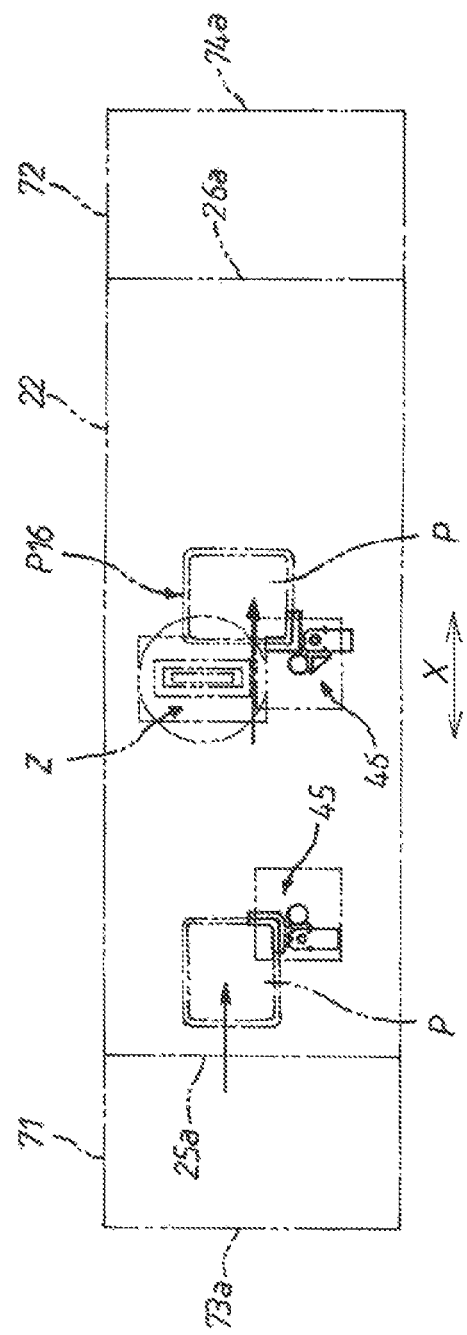
FIG. 19 is a process diagram 9 illustrating the operation of the chuck-slide device.

(Eighth process) In the eighth process, in FIG. 19, in the state in which the package P is gripped by the chuck member 46 at the corner portion P6, with the forward movement in the X-axis direction (movement to the front in the conveying direction of the package P) of the movable table 42b by the operation of the linear-motor table 42, the surfaces of at least ½ of the upper surface P11 and the lower surface P12 (half on the upper side in illustration) and the whole surface of the side surface P16 of the package P pass through the electron beam irradiation zone Z. In this eighth process, at least ½ of the surface of each of the upper surface P11 and the lower surface P12 and the whole surface of the side surface P16 of the package P are sterilized.

Therefore, by using the second process, the fourth process, the sixth process, and the eighth process at the same time, the whole surface of each of the upper surface P11 and the lower surface P12 and all the side surfaces P13, P14, P15, and P16 of the package P are sterilized. Here, the whole surface of each of the upper surface P11 and the lower surface P12 of the package P passes through the electron beam irradiation zone Z from the short distance twice.

At this time, in the rear in the conveying direction (left side in FIG. 19) of the package P, another package P in standby in the carrying-in pass box 71 is carried into the electron beam irradiation chamber 22 through the shutter 25a by the operation of the roller conveyer 51.

Figure 20:
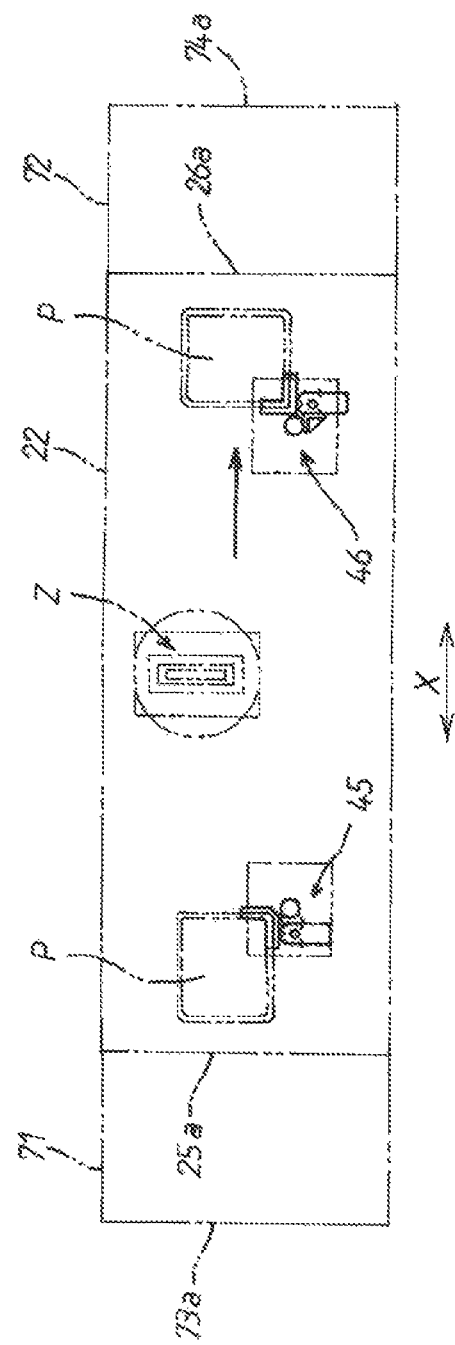
FIG. 20 is a process diagram 10 illustrating the operation of the chuck-slide device.

(Ninth process) In the ninth process, in FIG. 20, in the state in which the package P is gripped by the chuck member 46 at the corner portion P6, with the forward movement in the X-axis direction (movement to the front in the conveying direction of the package P) of the movable table 42b by the operation of the linear-motor table 42, the package P moves to an end portion of the roller conveyer 52 for carrying-out. Here, when the chuck 46b of the chuck member 46 releases the corner portion P6, the package P is delivered from the chuck member 46 to the roller conveyer 52.

At this time, in the rear in the conveying direction (left side in FIG. 20) of the package P, another package P having been carried into the electron beam irradiation chamber 22 in the eighth process is fixed at the fixed position by the operation of the positioning cylinder 60 on the front end portion of the roller conveyer 51 and gripped by the chuck 45b of the chuck member 45 at the corner portion P5.

As described above, by the operation of the chuck-slide device 40 in the first process to the ninth process, the whole surface of the package P is uniformly sterilized by the electron beam. Subsequently, the package P with the whole surface sterilized is carried out to the outside of the electron beam irradiation device 100 (into the aseptic work room) through the two shutters 26a and 74a of the carrying-out pass box 72 by the operation of the roller conveyer 52.

These processes are repeated, and the sequentially conveyed packages P are sterilized and conveyed into the aseptic work room. In the aseptic work room into which the package p is conveyed as above, the upper-surface seal is peeled open from the polyethylene tab of the package P, and a filling work is performed into the sterilized syringe therein.

As described above, in this embodiment, three units of the small-sized low-energy electron accelerator having the size of the irradiation window with the long side (width direction) of 145 mm and the short side (length direction) of 25 mm were employed and operated at the acceleration voltage of 70 kV. As a result, an absorbed dose of 15 kGy or more was found on any portion on the surface of the package P, and the sterilization level on the whole surface of the actual package P was enough to guarantee the level of SAL≤$10^{-6}$. From this fact, by using the electron beam irradiation device according to this embodiment, the sterilization level on the whole surface of the package P becomes substantially equal, and reliability and safety of the sterilization effect can be maintained high.

As described above, the electron beam irradiation device according to this embodiment employs the small-sized low-energy electron accelerator having the irradiation window narrower than the irradiated width of each of the upper surface and the lower surface of the package P and irradiates the electron beam from the upper side, the lower side, and one of the sides of the package P. Moreover, the chuck-slide device is employed, and uniform electron beam irradiation can be performed from the short distance on the whole surface of the package P. Moreover, since the electron beam can be uniformly irradiated from the short distance, the acceleration voltage of the small-sized low-energy electron accelerator can be kept low and operated.

Moreover, since the electron accelerator is operated with its acceleration voltage kept low, the quantities of the X-rays and ozone generated secondarily is decreased as compared with the prior-art electron beam irradiation device. Since the quantity of the generated X-rays is decreased, the outer wall portion of the electron beam irradiation device can be made of a stainless metal plate without employing a lead plate. Furthermore, since the quantity of the generated ozone is decreased, corrosion of the electron beam irradiation chamber and the machine chamber can be alleviated. Moreover, since the quantity of the generated ozone is decreased, intrusion of ozone into the package P is drastically reduced, and an influence on end products such as the syringes accommodated therein and a filling liquid to be filled in the syringe in a subsequent process is made small.

Moreover, in the electron beam irradiation device according to this embodiment, since the compact small-sized low-energy electron accelerator having the narrow irradiation window is employed, the electron beam irradiation device itself becomes compact, and the initial cost of the device including the cost of the electron accelerator can be kept low. Furthermore, in this embodiment, since the small-sized low-energy electron accelerator can be operated with a low acceleration voltage, the usage limit (life) of the electron accelerator is extended, and the maintenance cost of the device can be kept low.

Moreover, in this embodiment, since the chuck-slide device is employed, uniform electron irradiation can be performed from the short distance to the whole surface of the package P. In the usual case of the electron beam irradiation to the whole surface of the object of irradiation, a complicated mechanism combining three-axes movement in the X-axis/

Y-axis/Z-axis directions and rotational movement in the θ-axis direction is needed. On the other hand, in this embodiment, gripping and delivery of the package P by the chuck member, one-axis movement in the X-axis direction of the package P by the linear-motor table, and rotation in the θ-axis direction of the package P by the rotating member are combined.

As described above, in the chuck-slide device of this embodiment, uniform electron beam irradiation from the short distance can be performed to the whole surface of the package P only by a simple structure and a few driving portions. As a result, the electron beam irradiation device itself becomes further compact, and the initial cost and the maintenance cost of the device can be further kept low.

Moreover, in this embodiment, the electron beam irradiation device is provided with the carrying-in pass box and the carrying-out pass box before and after itself. As a result, the sterilized state inside the electron beam irradiation device is maintained, and leakage of the X-rays to the outside generated in the electron beam irradiation device can be prevented. Moreover, these pass boxes are provided with two shutters, respectively, and by controlling so that these shutters are not opened at the same time, the sterilized state inside the electron beam irradiation device can be maintained more stably and leakage of the X-rays generated in the electron beam irradiation device to the outside can be completely prevented.

Thus, in the present invention, the electron beam irradiation device which can uniformly irradiate the electron beam to the entire outer surface of the object of irradiation by using the small-sized low-energy electron accelerator with the narrow irradiation window, whereby the sterilization level at each portion can be made substantially equal and reliability and safety of the sterilization effect can be maintained high, and can keep the initial cost and the maintenance cost of the device low by extending the cost and the usage limit (life) of the electron accelerator.

In putting the present invention into practice, not limited to the above described embodiment, the following various variations can be cited:

(1) In the above described embodiment, the small-sized low-energy electron accelerator capable of adjusting the acceleration voltage within the range of 40 to 70 kV is employed, and the sterilization level of $SAL \leq 10^{-6}$ is guaranteed, but this is not limiting, and by adjusting a moving speed of the package by the chuck-slide device by employing the electron accelerator with higher acceleration voltage, various sterilization levels can be guaranteed. For example, by operating the electron accelerator at a higher acceleration voltage, the sterilization level of $SAL \leq 10^{-12}$ can be guaranteed.

(2) In the above-described embodiment, the whole surfaces of the upper surface and the lower surface of the package pass through the electron beam irradiation zone twice. On the other hand, the whole side surfaces of the package pass through the electron beam irradiation zone once. Therefore, in order to make the absorbed dose of the electron beam irradiated to the whole surface of the package substantially equal, an output of the electron accelerator for irradiating the electron beam to the upper surface and the lower surface of the package may be lowered than the output of the electron accelerator for irradiating the electron beam to the side surface of the package in operation. As a result, the usage limit (life) of the electron accelerator for irradiating the electron beam to the upper surface and the lower surface of the package can be extended.

(3) In the above-described embodiment, a stainless metal plate is employed for the outer wall portion of the electron beam irradiation device body, but this is not limiting, and considering the case of operation of the electron accelerator at a high acceleration voltage, a lead plate instead of the stainless metal plate may be employed for the outer wall portion of the electron beam irradiation device body.

(4) In the above-described embodiment, the linear-motor table is employed for movement in the X-axis direction of the chuck-slide device, but this is not limiting, and movement by a rotary motor and a gear mechanism may be employed.

(5) Though not explained in the above-described embodiment, by making the pressure inside of the electron beam irradiation chamber of the electron beam irradiation device negative with respect to the inside of the continuously provided aseptic work room, the aseptic state of the aseptic work room can be maintained more stably.

(6) In the above-described embodiment, a double-shutter method is employed. That is, the first carrying-in port and the second carrying-in port of the carrying-in pass box and the first carrying-out port and the second carrying-out port of the carrying-out pass box are all arranged linearly so as to be juxtaposed in the conveying direction of the package, and a shutter is provided at each of the carrying-in ports and the carrying-out ports. By executing control such that the shutters of each the carrying-in ports and the carrying-out ports arranged as above are not opened at the same time, the X-rays generated in the electron beam irradiation device is prevented from leaking to the outside. However, the arrangement of each of carrying-in ports and the carrying-out ports of the pass boxes is not limited to that, and a general double-crank method may be employed. That is, the first carrying-in port and the second carrying-in port of the carrying-in pass box and the first carrying-out port and the second carrying-out port of the carrying-out pass box are arranged so as to be orthogonal to each other. By bending the conveying direction of the package between each of the carrying-in ports and between each of the carrying-out ports as arranged above twice by 90 degrees, the X-rays generated in the electron beam irradiation device is prevented from leaking to the outside.

(7) In the above-described embodiment, the chuck claw of the chuck-slide device gripping the package is operated so as not to pass through the electron beam irradiation zone. However, this is not limiting, and it may be so configured that the chuck claw passes through the electron beam irradiation zone, and the portion is sterilized all the time. In this case, it is preferably configured such that the chuck claw passes through the electron beam irradiation zone without gripping the package, and the portion of the chuck claw in contact with the package is sterilized.

(8) In the above-described embodiment, an area of approximately a half of the upper surface and the lower surface of the package is operated so as to pass through the electron beam irradiation zone, and the chuck claw of the chuck-slide device does not pass through the electron beam irradiation zone. However, this is not limiting, and the width of the irradiation window of the electron accelerator may be increased so that the electron beam is irradiated to the whole surface of the upper surface and the lower surface of the package. In this case, the chuck claw of the chuck-slide device passes through the electron beam irradiation zone and is sterilized all the time.

REFERENCE SIGNS LIST

100 electron beam irradiation device
10 body frame
20 electron beam irradiation device body
22 electron beam irradiation chamber 23 decompression chamber
24 machine chamber
25 carrying-in port
26 carrying-out port
21, 21a to 21e outer wall portion
23a, 23b partition wall portion
23c, 23d slide opening portion
25a, 26a shutter
30 electron beam generating device
31, 32, 33 electron accelerator
31a, 32a, 33a irradiation window
40 chuck-slide device
41, 42 linear-motor table
41a, 42a bed
41b, 42b movable table
43, 44 rotating member
43a, 44a rotation base
43b, 44b rotation shaft
45, 46 chuck member
45a, 46a support portion
45b, 46b chuck claw
50 conveying device
51, 52 roller conveyer
60 positioning cylinder
61, 62 cylinder
61a, 62a base
71, 72 pass box
73 carrying-in port
74 carrying-out port
73a, 74a shutter
61b, 62b telescopic support
61c, 62c fixed claw
P package
P1 tab
P2 upper-surface seal
P3 to P6 corner portion
P11 upper surface
P12 lower surface
P13 to P16 side surface
θ rotation direction
X moving direction
Z electron beam irradiation zone

The invention claimed is:
1. An electron beam irradiation device comprising:
electron beam irradiation means forming an electron beam irradiation zone by generating an electron beam; and
gripping/moving means gripping a part of an object of irradiation and moving so that the object of irradiation passes through the electron beam irradiation zone, wherein
the electron beam irradiation means is composed of three electron accelerators, each having an upper surface, a lower surface, and one side surface of the object of irradiation as irradiated surfaces, and is provided with three irradiation windows located substantially in parallel so as to face these three irradiated surfaces, respectively;
the irradiation window faced with the upper surface or the lower surface of the object of irradiation among the three irradiation windows has an irradiation width of at least ½ of the whole width of the upper surface or the lower surface of the object of irradiation, respectively,
the irradiation window faced with the one side surface of the object of irradiation among the three irradiation windows has an irradiation width of at least the whole width of the one side surface of the object of irradiation;
the gripping/moving means is provided with two gripping mechanisms for gripping different portions of the object of irradiation, respectively, two moving mechanisms for moving the gripping mechanisms in a longitudinal direction, respectively, so that the object of irradiations gripped by the two gripping mechanisms, respectively, pass through the electron beam irradiation zone, and two rotation mechanisms for rotating the gripping mechanisms so that the objects of irradiation gripped by the two gripping mechanisms, respectively, are rotated;
when the object of irradiation is gripped by the first gripping mechanism, by operations of the first moving mechanism and the first rotation mechanism, a portion in the upper surface and the lower surface of the object of irradiation not including the portion gripped by the first gripping mechanism and a side surface among the side surface of the object of irradiation not including the portion gripped by the first gripping mechanism pass through the electron beam irradiation zone; and
when the object of irradiation is spaced away from the first gripping mechanism and is gripped by the second gripping mechanism, by operations of the second moving mechanism and the second rotation mechanism, a portion in the upper surface and the lower surface of the object of irradiation not including the portion gripped by the second gripping mechanism and a side surface among the side surfaces of the object of irradiation not including the portion gripped by the second gripping mechanism pass through the electron beam irradiation zone.
2. The electron beam irradiation device according to claim 1 wherein
the first gripping mechanism has position modifying means for modifying a position of the object of irradiation to an appropriate position in order to grip the object of irradiation.
3. The electron beam irradiation device according to claims 1 or 2, further comprising:
a carrying-in pass box for carrying the object of irradiation into the electron beam irradiation device;
first conveying means for conveying the unsterilized object of irradiation from outside the electron beam irradiation device to a gripping position of the first gripping mechanism through this carrying-in pass box;
a carrying-out pass box for carrying the object of irradiation out to outside the electron beam irradiation device; and
second conveying means for conveying the sterilized object of irradiation from a gripping position of the second gripping mechanism to outside the electron beam irradiation device through the carrying-out pass box.
4. The electron beam irradiation device according to claim 3, wherein
the carrying-in pass box has a first carrying-in port opened between an inside of the carrying-in pass box and an outside of the electron beam irradiation device and a second carrying-in port opened between the inside of the carrying-in pass box and an inside of the electron beam irradiation device;
the carrying-out pass box has a first carrying-out port opened between an inside of the carrying-out pass box and the inside of the electron beam irradiation device and a second carrying-out port opened between an inside of the carrying-out pass box and the outside of the electron beam irradiation device;

the first carrying-in port, the second carrying-in port, the first carrying-out port, and the second carrying-out port are provided with opening/closing doors, respectively; and the first carrying-in port, the second carrying-in port, the first carrying-out port, and the second carrying-out port are opened linearly with respect to a conveying direction of the object of irradiation with opening portions in parallel.

5. An electron beam irradiation device comprising:

electron beam irradiation means forming an electron beam irradiation zone by generating an electron beam; and gripping/moving means gripping a part of an object of irradiation and moving so that the object of irradiation passes through the electron beam irradiation zone, wherein the electron beam irradiation means is composed of three electron accelerators, each having an upper surface, a lower surface, and one side surface of the object of irradiation as irradiated surfaces, and is provided with three irradiation windows located substantially in parallel so as to face these three irradiated surfaces, respectively;

the irradiation window faced with the upper surface or the lower surface of the object of irradiation among the three irradiation windows has an irradiation width of at least ½ of the whole width of the upper surface or the lower surface of the object of irradiation, respectively, the irradiation window faced with the one side surface of the object of irradiation among the three irradiation windows has an irradiation width of at least the whole width of the one side surface of the object of irradiation;

the gripping/moving means is provided with the gripping mechanism for gripping different portions of the object of irradiation alternately, the moving mechanism for moving the gripping mechanism in a longitudinal direction, so that the object of irradiation gripped by the gripping mechanism, pass through the electron beam irradiation zone, and the rotation mechanism for rotating the gripping mechanism so that the object of irradiation gripped by the gripping mechanism, is rotated;

when the object of irradiation is gripped by the gripping mechanism, by operations of the moving mechanism and the rotation mechanism, a portion in the upper surface and the lower surface of the object of irradiation not including the portion gripped by the gripping mechanism and a side surface among the side surface of the object of irradiation not including the portion gripped by the gripping mechanism pass through the electron beam irradiation zone; and when the different portion of the object of irradiation is gripped by the gripping mechanism alternately, by operations of the moving mechanism and the rotation mechanism, a portion in the upper surface and the lower surface of the object of irradiation not including the portion gripped by the gripping mechanism and a side surface among the side surfaces of the object of irradiation not including the portion gripped by the gripping mechanism pass through the electron beam irradiation zone.

6. A method for electron beam irradiation of an object of irradiation that is a hexahedron composed of an upper surface, a lower surface, and four side surfaces, including:

a first process of gripping the object of irradiation by a first gripping mechanism;

a second process in which at least ½ of a surface of each of the upper surface and the lower surface and a whole surface of the first side surface of the object of irradiation pass through an electron beam irradiation zone by movement of a first moving mechanism in one direction;

a third process in which a first rotation mechanism rotates the first gripping mechanism by 90° and the object of irradiation gripped by the first gripping mechanism is rotated by 90° in a horizontal direction;

a fourth process in which at least ½ of the surface of each of the upper surface and the lower surface and the whole surface of the second side surface of the object of irradiation pass through the electron beam irradiation zone by movement of the first moving mechanism in the opposite direction;

a fifth process of gripping the object of irradiation by a second gripping mechanism and of separating the same away from the first gripping mechanism;

a sixth process in which at least ½ of the surface of each of the upper surface and the lower surface and the whole surface of the third side surface of the object of irradiation pass through the electron beam irradiation zone by movement of a second moving mechanism in one direction;

a seventh process in which a second rotation mechanism rotates the second gripping mechanism by 90° and the object of irradiation gripped by the second gripping mechanism is rotated by 90° in the horizontal direction;

an eighth process in which at least ½ of the surface of each of the upper surface and the lower surface and the whole surface of the fourth side surface of the object of irradiation pass through the electron beam irradiation zone by movement of the second moving mechanism in the opposite direction; and a ninth process of separating the object of irradiation away from the second gripping mechanism, wherein processes one through nine result in all surfaces of the object of irradiation being sterilized.

7. The method of claim 6, wherein in at least one process of the first to ninth processes, the gripped portion of the second gripping mechanism or each of the gripped portions of the first gripping mechanism and the second gripping mechanism passes through the electron beam irradiation zone.

* * * * *